(12) United States Patent
Abhari et al.

(10) Patent No.: US 10,717,687 B2
(45) Date of Patent: *Jul. 21, 2020

(54) EVEN CARBON NUMBER PARAFFIN COMPOSITION AND METHOD OF MANUFACTURING SAME

(71) Applicant: REG SYNTHETIC FUELS, LLC, Ames, IA (US)

(72) Inventors: Ramin Abhari, Bixby, OK (US); H. Lynn Tomlinson, Leonard, OK (US); Vladimir Gruver, Jenks, OK (US)

(73) Assignee: REG SYNTHETIC FUELS, LLC, Ames, IA (US)

( * ) Notice: Subject to any disclaimer, the term of this patent is extended or adjusted under 35 U.S.C. 154(b) by 31 days.

This patent is subject to a terminal disclaimer.

(21) Appl. No.: 15/973,064

(22) Filed: May 7, 2018

(65) Prior Publication Data
US 2018/0290946 A1 Oct. 11, 2018

Related U.S. Application Data

(60) Continuation of application No. 14/997,285, filed on Jan. 15, 2016, now Pat. No. 9,963,401, which is a
(Continued)

(51) Int. Cl.
*C07C 1/207* (2006.01)
*C07C 1/22* (2006.01)
(Continued)

(52) U.S. Cl.
CPC ............. *C07C 1/2078* (2013.01); *C07C 1/22* (2013.01); *C07C 9/14* (2013.01); *C07C 9/15* (2013.01);
(Continued)

(58) Field of Classification Search
CPC ............ C10G 3/00; Y02E 50/10; Y02E 50/13
(Continued)

(56) References Cited

U.S. PATENT DOCUMENTS 2,093,159 A 9/1937 Schmidt
2,163,563 A 6/1939 Schrauth
(Continued)

FOREIGN PATENT DOCUMENTS

CA 1313200 1/1993
CA 2149685 9/1999
(Continued)

OTHER PUBLICATIONS

"The 2001 Mixing, Blending and Size Reduction Handbook," Processing (Mar. 2001), 8 pages, available at http://www.admix.com/pdfs/resourcelibrary-tech-mixhandbook.pdf.
(Continued)

*Primary Examiner* — Nina Bhat
(74) *Attorney, Agent, or Firm* — Foley & Lardner LLP

(57) ABSTRACT

Paraffin compositions including mainly even carbon number paraffins, and a method for manufacturing the same, is disclosed herein. In one embodiment, the method involves contacting naturally occurring fatty acid/glycerides with hydrogen in a slurry bubble column reactor containing bimetallic catalysts with equivalent particle diameters from about 10 to about 400 micron. The even carbon number compositions are particularly useful as phase change material.

22 Claims, 7 Drawing Sheets

Related U.S. Application Data continuation of application No. 13/466,813, filed on May 8, 2012, now abandoned, which is a division of application No. 12/331,906, filed on Dec. 10, 2008, now Pat. No. 8,231,804.

(51) Int. Cl.
- *C09K 5/06* (2006.01)
- *C07C 9/14* (2006.01)
- *C07C 9/22* (2006.01)
- *C10L 1/04* (2006.01)
- *C07C 9/15* (2006.01)

(52) U.S. Cl.
CPC ............... *C07C 9/22* (2013.01); *C09K 5/063* (2013.01); *C10L 1/04* (2013.01); *C07C 2521/02* (2013.01); *C07C 2521/04* (2013.01); *C07C 2523/882* (2013.01); *C07C 2523/883* (2013.01); *C07C 2523/888* (2013.01); *C07C 2525/00* (2013.01); *C07C 2525/02* (2013.01); *C07C 2527/18* (2013.01)

(58) Field of Classification Search
USPC .................. 585/240–242, 13–14; 44/605
See application file for complete search history.

(56) References Cited

U.S. PATENT DOCUMENTS

| | | |
|---|---|---|
| 2,482,760 A | 9/1949 | Goebel |
| 2,482,761 A | 9/1949 | Goebel |
| 2,664,429 A | 12/1953 | Goebel |
| 2,793,220 A | 5/1957 | Barrett et al. |
| 2,915,447 A | 12/1959 | Arabian |
| 3,144,404 A | 8/1964 | Tyson |
| 3,363,022 A | 1/1968 | Harrison et al. |
| 3,496,099 A | 2/1970 | Bridge |
| 3,505,418 A | 4/1970 | Jubin |
| 3,903,191 A | 9/1975 | Pollitzer |
| 3,979,470 A | 9/1976 | Firnhaber et al. |
| 4,049,686 A | 9/1977 | Ringers et al. |
| 4,151,072 A | 4/1979 | Nowack et al. |
| 4,233,140 A | 11/1980 | Antonelli et al. |
| 4,252,634 A | 2/1981 | Khulbe et al. |
| 4,300,006 A | 11/1981 | Nelson |
| 4,300,009 A | 11/1981 | Haag et al. |
| 4,431,524 A | 2/1984 | Norman |
| 4,432,865 A | 2/1984 | Norman |
| 4,451,689 A | 5/1984 | Pasky |
| 4,512,878 A | 4/1985 | Reid et al. |
| 4,554,397 A | 11/1985 | Stern et al. |
| 4,571,442 A | 2/1986 | Cosyns et al. |
| 4,594,172 A | 6/1986 | Sie |
| 4,698,185 A | 10/1987 | Dijkstra et al. |
| 4,734,226 A | 3/1988 | Parker et al. |
| 4,746,420 A | 5/1988 | Darian et al. |
| 4,913,794 A | 4/1990 | Le et al. |
| 4,937,051 A | 6/1990 | Graven et al. |
| 4,952,306 A | 8/1990 | Sawyer et al. |
| 4,960,960 A | 10/1990 | Harrison et al. |
| 4,992,605 A * | 2/1991 | Craig ................... C10L 1/04 44/389 |
| 5,037,528 A | 8/1991 | Garwood et al. |
| 5,093,535 A | 3/1992 | Harrison et al. |
| 5,105,015 A | 4/1992 | Lin et al. |
| 5,135,638 A | 8/1992 | Miller |
| 5,146,022 A | 9/1992 | Buchanan et al. |
| 5,180,868 A | 1/1993 | Baker et al. |
| 5,239,096 A | 8/1993 | Rohdenburg et al. |
| 5,292,428 A | 3/1994 | Harrison et al. |
| 5,298,639 A | 3/1994 | Toeneboehn et al. |
| 5,346,724 A | 9/1994 | Ohgake et al. |
| 5,378,348 A | 1/1995 | Davis et al. |
| 5,475,160 A | 12/1995 | Singleton et al. |
| 5,502,077 A | 3/1996 | Breivik et al. |
| 5,578,090 A | 11/1996 | Bradin |
| 5,647,226 A | 7/1997 | Scaringe et al. |
| 5,688,749 A | 11/1997 | Ibuki et al. |
| 5,705,722 A | 1/1998 | Monnier et al. |
| 5,851,338 A | 12/1998 | Pushaw |
| 5,877,358 A | 3/1999 | Garton et al. |
| 5,882,505 A | 3/1999 | Wittenbrink et al. |
| 5,906,729 A | 5/1999 | Chou |
| 6,096,690 A | 8/2000 | Wittenbrink et al. |
| 6,123,835 A | 9/2000 | Ackerson et al. |
| 6,150,575 A | 11/2000 | Angevine et al. |
| 6,185,742 B1 | 2/2001 | Doherty |
| 6,187,903 B1 | 2/2001 | Elsasser et al. |
| 6,190,535 B1 | 2/2001 | Kalnes et al. |
| 6,194,625 B1 | 2/2001 | Graves et al. |
| 6,203,695 B1 | 3/2001 | Harle et al. |
| 6,399,845 B1 | 6/2002 | Raulo et al. |
| 6,402,935 B1 | 6/2002 | Kalnes |
| 6,458,265 B1 | 10/2002 | Miller et al. |
| 6,574,971 B2 | 6/2003 | Suppes |
| 6,613,404 B2 | 9/2003 | Johnson |
| 6,635,595 B2 | 10/2003 | Kaimal et al. |
| 6,638,418 B1 | 10/2003 | Kalnes et al. |
| 6,660,812 B2 | 12/2003 | Kuechler et al. |
| 6,787,022 B1 | 9/2004 | Berlowitz et al. |
| 6,833,064 B2 | 12/2004 | Berlowitz et al. |
| 6,846,778 B2 | 1/2005 | Johnson et al. |
| 6,855,410 B2 | 2/2005 | Buckley |
| 6,858,048 B1 | 2/2005 | Jimeson et al. |
| 7,232,935 B2 | 6/2007 | Jakkula et al. |
| 7,288,685 B2 | 10/2007 | Marker |
| 7,511,181 B2 | 3/2009 | Petri et al. |
| 7,550,634 B2 | 6/2009 | Yao et al. |
| 7,691,159 B2 | 4/2010 | Li |
| 7,718,051 B2 | 5/2010 | Ginosar et al. |
| 7,754,931 B2 | 7/2010 | Monnier et al. |
| 7,816,570 B2 | 10/2010 | Roberts et al. |
| 7,836,722 B2 | 11/2010 | Magill et al. |
| 7,846,323 B2 | 12/2010 | Abhari et al. |
| 7,851,663 B2 | 12/2010 | Abhari |
| 7,888,418 B2 | 2/2011 | Connell et al. |
| 7,928,273 B2 | 4/2011 | Bradin |
| 7,960,597 B2 | 6/2011 | Miller |
| 7,968,757 B2 | 6/2011 | Abhari et al. |
| 7,982,076 B2 | 7/2011 | Marker et al. |
| 8,003,836 B2 | 8/2011 | Marker et al. |
| 8,022,258 B2 | 9/2011 | Myllyoja et al. |
| 8,026,401 B2 | 9/2011 | Abhari et al. |
| 8,187,344 B2 | 5/2012 | Jakkula et al. |
| 8,212,094 B2 | 7/2012 | Myllyoja et al. |
| 8,231,804 B2 | 7/2012 | Abhari |
| 8,278,492 B2 | 10/2012 | Myllyoja et al. |
| 8,581,013 B2 | 11/2013 | Abhari et al. |
| 8,629,308 B2 | 1/2014 | Abhari et al. |
| 2002/0062053 A1 | 5/2002 | Berlowitz et al. |
| 2004/0055209 A1 | 3/2004 | Jakkula et al. |
| 2004/0067856 A1 | 4/2004 | Johnson et al. |
| 2004/0170806 A1 | 9/2004 | Hittle et al. |
| 2004/0230085 A1 | 11/2004 | Jakkula et al. |
| 2005/0004239 A1 | 1/2005 | Bull et al. |
| 2005/0150815 A1 | 7/2005 | Johnson et al. |
| 2006/0006098 A1 | 1/2006 | Espinoza et al. |
| 2006/0100473 A1 | 5/2006 | Grootjans et al. |
| 2006/0161032 A1 | 7/2006 | Murzin et al. |
| 2006/0186020 A1 | 8/2006 | Gomes |
| 2006/0199984 A1 | 9/2006 | Kuechler et al. |
| 2006/0199988 A1 | 9/2006 | Kowalik et al. |
| 2006/0207166 A1 | 9/2006 | Herskowitz et al. |
| 2006/0264684 A1 | 11/2006 | Petri et al. |
| 2007/0006523 A1 | 1/2007 | Myllyoja et al. |
| 2007/0010682 A1 | 1/2007 | Myllyoja et al. |
| 2007/0026012 A1 | 2/2007 | Delisa et al. |
| 2007/0131579 A1 | 6/2007 | Koivusalmi et al. |
| 2007/0135669 A1 | 6/2007 | Koivusalmi et al. |
| 2007/0161832 A1 | 7/2007 | Myllyoja et al. |
| 2007/0170091 A1 | 7/2007 | Monnier et al. |
| 2007/0187291 A1 | 8/2007 | Miller et al. |
| 2007/0197667 A1 | 8/2007 | Vogel |

(56) References Cited

U.S. PATENT DOCUMENTS

| | | | |
|---|---|---|---|
| 2007/0260102 A1* | 11/2007 | Duarte Santiago | C10G 45/00 585/733 |
| 2008/0308458 A1 | 12/2008 | Dindi et al. | |
| 2008/0312346 A1 | 12/2008 | McCall et al. | |
| 2008/0312480 A1 | 12/2008 | Dindi et al. | |
| 2009/0065396 A1 | 3/2009 | Kokayeff et al. | |
| 2009/0077866 A1 | 3/2009 | Kalnes et al. | |
| 2010/0249485 A1 | 9/2010 | Mdleleni et al. | |
| 2010/0292518 A1 | 11/2010 | Debuisschert et al. | |
| 2011/0152588 A1 | 6/2011 | Kothandaraman et al. | |
| 2012/0157726 A1 | 6/2012 | Vauk et al. | |
| 2012/0165581 A1 | 6/2012 | Dupassieux et al. | |
| 2012/0251424 A1 | 10/2012 | Havlik et al. | |

FOREIGN PATENT DOCUMENTS

| | | |
|---|---|---|
| CZ | 283575 | 5/1998 |
| DE | 41 16 905 | 8/1992 |
| EP | 0 195 991 | 10/1986 |
| EP | 0 412 785 | 2/1991 |
| EP | 0 794 241 | 3/1997 |
| EP | 1 396 531 A2 | 3/2004 |
| EP | 1 728 844 | 12/2006 |
| EP | 1 741 768 | 1/2007 |
| FI | 72435 | 2/1987 |
| FI | 73367 | 6/1987 |
| FI | 89073 | 4/1993 |
| FI | 95391 | 1/1996 |
| FR | 2607803 | 6/1988 |
| GB | 1 061 644 | 3/1967 |
| GB | 2 090 611 | 7/1982 |
| IE | 921671 | 12/1995 |
| JP | 59-108088 | 6/1984 |
| JP | 07-300593 | 11/1995 |
| SE | 9700149 | 8/1997 |
| SE | 520633 | 8/2003 |
| SG | 172045 | 11/2012 |
| WO | WO-00/11117 | 3/2000 |
| WO | WO-00/29512 | 5/2000 |
| WO | WO-01/49812 | 7/2001 |
| WO | WO-03/022960 A2 | 3/2003 |
| WO | WO 2004/026161 | 4/2004 |
| WO | WO-2004/104142 | 12/2004 |
| WO | WO-2005/026297 | 3/2005 |
| WO | WO-2006/100584 | 9/2006 |
| WO | WO-2007/003708 A1 | 1/2007 |
| WO | WO-2007/063874 | 6/2007 |
| WO | WO-2007/068795 | 6/2007 |
| WO | WO-2008/027699 | 3/2008 |
| WO | WO-2008/054442 | 5/2008 |
| WO | WO-2008/058664 | 5/2008 |
| WO | WO-2008/067627 | 6/2008 |
| WO | WO-2009/085686 | 7/2009 |
| WO | WO-2009/117337 | 9/2009 |
| WO | WO-2009/151692 | 12/2009 |

OTHER PUBLICATIONS

Abhari et al., "New Routes to Ethylene," EEPC Seminar in Berlin, Germany, Oct. 20-22, 2010, pp. 1-38.

Affens, et al., "Effect of Composition on Freezing Points of Model Hydrocarbon Fuels," presented before the Division of Fuel Chemistry, American Chemical Society, New York, Aug. 1981, 9 pages, available at https://web.anl.gov/PCS/acsfuel/preprint%20archive/Files/26_3_NEW%20YORK_08-81_0178.pdf (subsequently published in Fuel, 63(4), Apr. 1984, pp. 543-547).

Akzo Nobel Catalyst Presentation, Oct. 2003 (63 pages).

Alencar, J.W., et al., Pyrolysis of Tropical Vegetable Oils, J. Agric. Food Chem., vol. 31, 1983, pp. 1268-1270.

Ali et al., "Fuel Properties of Tallow and Soybean Oil Esters," JAOCS, 1995, vol. 72, No. 12.

Ali, et al., "Mineral Composition, Quality and Physico-chemical Parameters of the Local Tallow of Pakistan," Pakistan Journal of Nutrition, 7(5): 717-720, 2008.

Amended Declaration of Dr. Michael T. Klein.

Amended Petition for Inter Partes Review No. IPR2013-00578 (U.S. Pat. No. 8,231,804) dtd Sep. 20, 2013.

American Petroleum Institute, Properties of Hydrocarbons of High Molecular Weight Synthesized by Research Project 42 of the American Petroleum Institute (1967).

Antoniassi, R. et al, "Pretreatment of Corn Oil for Physical Refining," JAOCS, vol. 75, No. 10, 1998, pp. 1411-1415.

Applicant Amendment and Response, dated Jan. 23, 2012, U.S. Pat. No. 8,231,804 File History. (Ex. 2033 in IPR2013-00578).

Arca, M., et al., Evidence Contrary to the Accepted Diels-Alder Mechanism in the Thermal Modification of Vegetable Oils, J. Am. Oil Chem. Soc., 89 (2012), pp. 987-994.

Arroyo et al., "Hydrocracking and isomerization of n-paraffin mixtures and a hydrotreated gasoil on Pt/ZSM-22: confirmation of pore mouth and key013lock catalysis in liquid phase," Applied Catalysis A: General 192, 2000, pp. 9-22.

ASTM International, "Standard Specification for Diesel Fuel Oil", Designation: D975-12, printed Nov. 9, 2012, 26 pages.

ASTM International, Designation: D6751-11b, "Standard Specification for Biodiesel Fuel Blend Stock (B100) for Middle Distillate Fuels," Jul. 2011, pp. 1083-1091.

*AT& T Corp. v. Microsoft Corp.*, 2004 WL 292321, 2004 U.S. Dist. LEXIS 2192(S.D.N.Y. Feb. 17, 2004). (Ex. 2036 in IPR2013-00578).

B. Lee, et al., "Bioremediation and Ecotoxicity of Drilling Fluids Used for Land-based Drilling," AADE Technical Conference, Houston, Apr. 2002, pp. 1-12.

B.B. He and J. Van Gerpen "Biodiesel Quality Affected by Sulfur Content Originated by Different Feedstocks and a Database for the Same" Final Report KLK432 N08-04, National Institute for Advanced Transportation Technology, University of Idaho (Feb. 2008).

Batts et al., "A Literature Review on Fuel Stability Studies with Particular Emphasis on Diesel Oil", Energy & Fuels, 1991, vol. 5, pp. 2-21.

Beare-Rogers, J. et al, "Lexicon of Lipid Nutrition," Pure and Applied Chemistry, vol. 73, No. 4, 2001, pp. 685-744.

Bell, et al., "Biodiesel," TEAM Report for Imperial Oil, Queen's University, Kingston, Ontario, Apr. 2007. (106 pages).

Bergerioux, C. et al, "Determination of Trace Element Pathways in a Petroleum Distillation Unit by Instrumental Neutron Activation Analysis," Journal of Radioanalytical Chemistry, vol. 54, No. 1-2,1979, pp. 255-265.

Bradley, T.F., et al., Drying Oils and Resins, Ind. & Eng. Chem., vol. 32, No. 6, 1940, pp. 802-809.

Burch et al., "Melting-Point Models of Alkanes", J. Chem. Eng. Data 2004, 49, 858-863.

Calculation of Relative Response Factors.

Calculation of Weight Percents from Table 9 of Craig.

Canada Centre for Mineral and Energy Technology, "New Process Yields Cleaner Diesel", Canmet'95: New Directions, 1995, p. 14.

Canakci et al., "Biodiesel Production from Oils and Fats with High Free Fatty Acids", Transactions of the ASAE, 2001, vol. 44(6), pp. 1429-1436.

CanmetENERGY's SuperCetane Technology, Natural Resources Canada, http://cetcvareness.nrcan.gc.ca/eng/industrialprocesses/industrialenergysystems, Nov. 2008, Accessed Jul. 19, 2013 (4 pages).

Catalysts in Petroleum Refining & Petrochemicals Program Listing, 16th Saudi-Japanese Symposium, http://www3.kfupm.edu.sa/catsymp/Symp 16th/Program.htm, accessed Sep. 9, 2013.

Chaurasia, et al., "Quantitation of Fatty Acids and Hydroxy Fatty Acids by Gas Chromatography/Mass Spectrometry. Predictively Useful Correlations of Relative Response Factors with Empirical Formula," Journal of Mass Spectrometry, 30:1018-1022 (1995). (Ex. 2024 in IPR2013-00578).

Clements, L.D., "Blending Rules for Formulating Biodiesel Fluid.", Proceedings of the Third Liquid Fuels Conference, Sep. 15-17, 1996, pp. 44-53.

(56) References Cited

OTHER PUBLICATIONS

Cmolik et al., "Effects of plant-scale alkali refining and physical refining on the quality of rapeseed oil", Eur. J. Lipid Sci. Technol. 2000, 15-22.
Communication dated May 26, 2014 from the Technische Informationsbibliothek und Universitätsbibliothek Hannover, Germany. English translation included -3 pages (Ex. 2039 in IPR2013-00578).
Compilation of e-mail correspondence between Mr. Abhari and Southwest Research Institute ("SwRI") ending Mar. 7, 2008. (Ex. 2011 in IPR2013-00578).
Compilation of Email Correspondence Between Syntroleum and AG Equipment Co., Jul. 22, 2008 to Oct. 24, 2008. (Ex. 2015 in IPR2013-00578).
Compilation of SwRI GC Test Data (Feb. 26, 2008-Jul. 7, 2008). (Ex. 2013 in IPR2013-00578).
Compilation of Syntroleum GC Test Reports dated from Jun. 4, 2007 through Aug. 3, 2007. (Ex. 2007 in IPR2013-00578).
Connor, et al., "Hydrogenolysis of Oxygenated Organic Compounds," J. Am. Chem. Soc., 54(12), 1932, pp. 4678-4690.
Cooper et al., "Production of Swedish Class I Diesel Using Dual-Stage Process", Catalytic Hydroprocessing of Petroleum and Distillates, based on Proceedings of the AIChE Spring National Meeting, Houston, Texas, Mar. 28-Apr. 1, 1993, 279-290.
Corma, et al., "Transformation of Alkanes on Solid Acid and Bifunctional Catalysts", Catalytic Activation and Functionalisation of Light Alkanes: Advances and Challenges, Editors E.G. Derouane et al., 1998, Netherlands: Kluwer Academic Publishers, vol. 44, pp. 35-74.
Craig, et al., "A Marketing Survey of Worldwide Potential for Use of Vegetable Oil Conversion Products in Diesel Fuel," Saskatchewan Research Council, Oct. 1989 (182 pages).
Criterion, "Technical Bulletin: CRITERION* Hydrotreating Catalyst In-Situ Presulphiding Guidelines—Liquid Phase (Preferred method)—Gase Phase (alternative method)" Criterion Catalysts, Aug. 1998, 1-9.
Curriculum Vitae of Dr. H. Henry Lamb, Revised May 27, 2014. (Ex. 2021 in IPR2013-00578).
Curriculum Vitae of Dr. Michael T. Klein.
D.V. Hale, et al, "Phase Change Materials Handbook," NASA Contractor Report 61363, Sep. 1971, 204 pages.
Declaration of U.S. Pat. No. 8,231,804 Patent Inventor, Mr. Ramin Abhari, May 27, 2014. (Ex. 2001 in IPR2013-00578).
Declaration of Jaques Monnier under 37 C.F.R. 1.132, dated Jan. 7, 2010, filed in U.S. Appl. No. 11/234,175, which issued as Monnier '931.
Declaration of Jukka Myllyoja, Mar. 11, 2009, U.S. Pat. No. 8,022,258 File History. (Ex. 2027 in IPR2013-00578).
Declaration of Pekka Aalto, Nov. 14, 2012, U.S. Pat. No. 8,187,344 File History. (Ex. 2028 in IPR2013-00578).
Deem, A.G. et al, "Catalytic Poisoning in Liquid-Phase Hydrogenation," Industrial and Engineering Chemistry, vol. 33, No. 11, Nov. 1941, pp. 1373-1376.
Del Gallo et. al. "Comparison of the Effects of Nitrogen Poisoning on Molybdenum Oxycarbide and Pt/B-Zeolite Catalysts in the Isomerization of n-Heptane," Ind. Eng. Chem. Res., 1996, vol. 35, No. 10, pp. 3302-3310.
Derrien et al., "The IFP Selective Hydrogenation Process", Chemical Engineering Process, vol. 70, No. 1, Jan. 1974, 74-80.
Doty, D.M. (1971). "Removal of Polyethylene and Other Polymeric Materials from Rendered Animal Fat." The Director's Digest, Fats and Proteins Research Foundation, Inc., 90, 4 pgs.
Dr. Lamb's Calculation of Weight Percentages from Craig, May 27, 2014.(Ex. 2029 in IPR2013-00578).
Duncan, D.P. in "Naval Stores," Zinkel, et al., Editors, Pulp Chemicals Association, New York, 1989, pp. 388-389.
Dynamic Fuels, "About", http://www.dynamicfuelsllc.com/. Accessed Nov. 12, 2012, 8 pages.
Dynamic Fuels, "Compare", http://www.dynamicfuelsllc.com/. Accessed Nov. 12, 2012, 7 pages.
Dynamic Fuels, "Frequently Ask Questions," http://dynamicfuelsllc.com/wpnews/frequently-ask-questions/, Accessed Nov. 12, 2012, 4 pages.
Edgar et al., "Analysis is key to hydrotreater troubleshooting", Oil & Gas Journal, vol. 82, issue 23, Jun. 4, 1984, 67-70.
Egeberg et al., "Hydrotreating in the Production of Green Diesel," Digital Refining, Apr. 2010, 13 pages; Available for download at http://www.digitalrefining.com/article/1000156,Hydrotreating_in_the_production_of_green_diesel.html#.UcSCEKybWVo.
Egeberg, et al., "Novel Hydrotreating Technology for Production of Green Diesel," 14th European Refining Technology Conference, Berlin, Germany, Nov. 9-11, 2009, 21 pages.
Elliott, et al., "Hydrodeoxygenation of Wood-Derived Liquids to Produce Hydrocarbon Fuels," Proceedings of the 20th Intersociety Energy Conversion Engineering Conf., vol. 1 of 3, 1985. (9 pages).
E-mail string ending Dec. 6, 2007 between Mr. Abhari and Intertek PARC regarding pilot plant testing. (Ex. 2010 in IPR2013-00578).
Erickson et al., "Soybean Oil Modern Processing and Utilization", American Soybean Association, 1990, 20 pages.
European Committee for Standardization (CEN), "Automotive fuels—Paraffinic diesel from synthesis or hydrotreatment—Requirements and test methods," TC WI WS038: 2009 (E), 10 pages.
European Food Safety Authority, "Scientific Opinion on the re-evaluation of candelilla wax (E 902) as a food additive," EFSA Journal 2012;10(11): 2946 (published Jan. 28, 2013), 27 pages.
European Standard EN 590:2004, "Automotive Fuels—Diesel—Requirements and Test Methods," Swedish Standards Institute, 2004, English version, available at http://www.repsol.com/imagenes/es_gl/EN%20590_04_93548_tcm10-67163.pdf, 13 pages.
Examiner Interview Summary, dated Jan. 24, 2012, U.S. Pat. No. 8,231,804 File History. (Ex. 2035 in IPR2013-00578).
Excerpted pages from Jul. 9, 2008 PowerPoint Presentation to Dynamic Fuels Management Committee. (Ex. 2016 in IPR2013-00578).
Excerpts of Documents Provided by Doosan Mecatec Co. Regarding Fabrication of Geismar Plant, 2008. (Ex. 2014 in IPR2013-00578).
Expert Declaration of Dr. H. Henry Lamb, May 27, 2014. (Ex. 2020 in IPR2013-00578).
ExxonMobil Chemical, "Product Safety Summary—ISOPARM M Fluid," 2011, 3 pages.
ExxonMobil, "Material Safety Data Sheet—ISOPAR M Fluid," 2002 (Revised 2007, 2008), 10 pages.
Feng et al., "Chemical Composition of Tall-Oil Based Cetane Enhancer for Diesel Fuels", First Biomass Conference of The Americas: Energy, Environment, Agriculture, and Industry, Aug. 30-Sep. 2, 1993. 14 pages.
Ferrari, M. et al. "Hydrotreatment and Hydrocracking of Oil Fractions," Elsevier Science, pp. 85-95, 1999.
File History of U.S. Appl. No. 08/269,090 to Monnier et al. (filed Jun. 30, 1994) (abandoned).
File History of U.S. Appl. No. 08/517,421 to Monnier et al. (filed Aug. 21, 1995) (continuation-in-part), which issued as Monnier '722.
Filho et al., Catalytic Conversion of Hevea brasiliensis and Virola sebifera Oils to Hydrocarbon Fuels, JAOCS, vol. 69, No. 3, Mar. 1992, 266-271.
Filter Manufacturers Council, "Solving Winter Diesel Fuel / Fuel Filter Problems," Technical Service Bulletin 91-1R3, 1991 (Revised 2006), available at http://www.hastingsfilter.com/Literature/TSB/91-1R3.pdf, 2 pages.
Final Office Action in U.S. Appl. No. 13/742,991 dated Jun. 25, 2013 (18 pages).
Final Written Decision in Inter Partes Review No. IPR2013-00578 (U.S. Pat. No. 8,231,804)dated Mar. 12, 2015 (38 pages).
Food Fats and Oils, Inst. of Shortening and Edible Oils, 335-354 (9th Ed. 2006).
Formo, M.W., Ester Reactions of Fatty Materials, J. Am. Oil Chem. Soc., vol. 31, 1954, pp. 548-559.
Galeana et al., "Thermodynamics of Wax Precipitation in Petroleum Mixtures," AIChE Journal, 1996, vol. 42, No. 1, pp. 239-248.

(56) References Cited

OTHER PUBLICATIONS

Galperin, "Hydroisomerization of N-decane in the presence of sulfur and nitrogen compounds," Applied Catalysis A: General, 209, 2001 pp. 257-268.

Garrido et al., "Concentrations of Metal in vegetable edible oils", Food Chemistry, vol. 50, 1994, 237-243.

Ghosh, et al., "Detailed Composition-Based Model for Predicting the Cetane Number of Diesel Fuels," Ind. Eng. Chem. Res. 2006, 45, 346-351.

Goering et al., "Fuel Properties of Eleven Vegetable Oils," Transactions of the ASAE, 1982, pp. 1472-1477, 1483.

Goodfellow, J., "Animal Fat-Based Biodiesel: Explore Its Untapped Potential," Biodiesel Magazine, Feb. 10, 2009 (1 page).

Goodfellow, J., "Biofuel Production From Animal Fats: A North American Perspective," Sanimax Energy (23 pages).

Goodrum et al., "Rheological Characterization of Yellow Grease and Poultry Fat," JAOCS, 2002, vol. 79, No. 10, pp. 961-964.

Göröcs, et al., "The Determination of GC013MS Relative Molar Responses of Some n-Alkanes and their Halogenated Analogs," Journal of Chromatographic Science, 51:138-145 (2013). (Ex. 2023 in IPR2013-00578).

Gorshteyn, et al., "ExxonMobil Catalytic Dewaxing—A Commercial Proven Technology," Paper presented at the 2nd Russian Refining Technology Conference, Moscow, Sep. 26-27, 2002, 13 pages.

Gosselink, et al., "Mild Hydrotracking: Coping with Catalyst Deactivation," 34 Catalyst Deactivation, 279-287 (1987).

Griesbaum, et al., "Hydrocarbons," Ullmann's Encyclopedia of Industrial Chemistry, 2000, 61 pages.

Groschen, R., "Overview of: The Feasibility of Biodiesel from Waste/Recycled Greases and Animal Fats", Marketing Services Division, Minnesota Department of Agriculture, Oct. 2002, 28 pages.

Gunstone, F.D., et al., "The Lipid Handbook," Ch. 3 & 6, Chapman & Hall, Second Edition, 1994.

Gusmao et al., "Utilization of Vegetable Oils as an Alternative Source for Diesel-Type Fuel," Catalysis Today, 5, 1989, pp. 533-544.

Haas, M., "Animal Fats," Bailey's Industrial Oil and Fat Products, 6th Ed., vol. 1: Edible Oil and Fat Products: Chemistry, Properties, and Health Effects, 2005, pp. 161-212.

Hammami, et al., "Cloud Points: Can We Measure or Model Them?" Petroleum Science and Technology, vol. 21, Nos. 3 & 4, 2003, pp. 345-358.

Held, et al., "Production of Hydrocarbons from Biomass," Energy from Biomass: 3rd E.C. Conference, International Conference on Biomass, Venice, 1985 (7 pages).

Herrera et al., "Catalyst Selection for Hydrotreating Diesel Fuel from Residue Hydrocracking", ACS Preprints, 1992, vol. 37, No. 4, pp. 1855-1863.

Hill, C., An Introduction to Chemical Engineering Kinetics & Reactor Design, John Wiley & Sons, Inc., 1977, pp. 349-380, 382-387.

Himran, et al., Characterization of Alkanes and Paraffin Waxes for Application as Phase Change Energy Storage Medium, Energy Sources vol. 16, 1994 pp. 117-128.

Holmgren, et al., "New Developments in Renewable Fuels Offer More Choices", Hydrocarbon Processing, Sep. 2007, pp. 67-72.

Huber, et al., "Synergies between Bio- and Oil Refineries for the Production of Fuels from Biomass," Agnew. Chem. Int. Ed. 2007, 46, 7184-7201.

Iki, et al., "Applicability of Hydrogenated Palm Oil for Automotive Fuels", 16th Saudi Arabia-Japan Joint Symposium, Dhahran, Saudi Arabia, Nov. 5-6, 2006, 10 pages.

Iki, et al., "Vegetable Oil Hydrogenating Process for Automotive Fuel," SAE Technical Paper, Jul. 23, 2007, pp. 1871-1876.

J. Johnson, et al. "Emissions from Fischer-Tropsch Diesel Fuels" SAE Technical Paper 2001-01-3518 (published Sep. 24, 2001) ("SAE 2001").

Jennings, et al., "Experimental solubility data of various n-alkane waxes: effects of alkane chain length, alkane odd versus even carbon number structures, and solvent chemistry solubility," Fluid Phase Equilibria, 227, 2005, pp. 27-35.

Kalnes, et al.; Provisional U.S. Appl. No. 60/973,788, entitled "Production of Diesel Fuel from Biorenewable Feedstocks", filed Sep. 9, 2007.

Kent, J., "Table 8.2", Riegel's Handbook of Industrial Chemistry, 9th Edition, 1992, pp. 278-279.

Kirk-Othmer, "Concise Encyclopedia of Chemical Technology," John Wiley & Sons, Inc., New York NY, pp. 367-369,(1985). (Ex. 2030 in IPR2013-00578).

Kirk-Othmer, "Gravity Concentration to Hydrogen Energy", Encyclopedia of Chemical Technology, Third Edition, vol. 12, Copyright 1980 by John Wiley & Sons, Inc., 931-937.

Klimisch et al., "Paraffinic Naphthas", American Petroleum Institute, May 20, 2003, 41 pages.

Kriz, et al., "Catalysts for the Isomerization of C7 Paraffins," Ind. Eng. Chem. Res., 1998, 37:4560-4569.

Kubicka, et al., "Transformation of Plant Oils to Hydrocarbons," APROCHEM 2007, 1149-1155, Apr. 16-18, 2007.

L.G. Huve "Shell Global Solutions Dewaxing Technologies & Catalysts Current Status" pp. 1-13., 2007.

Lab notebook page prepared by Ramin Abhari (Feb. 20, 2008). (Ex. 2002 in IPR2013-00578).

Lange, N.A., "Lange's Handbook of Chemistry," (Ed. Dean, J.A.), Thirteenth Edition, 1985, pp. 7.375 & 7.626.

Latondress, E.G., "Refining, Bleaching and Hydrogenating Meat Fats," JAOCS, vol. 62, No. 4, 1985, pp. 812-815.

Laurent, et al., "Study of the hydrodeoxygenation of carbonyl, carboxylic and guaiacyl groups over sulfided CoMo/ γ-Al2O3 and NiMo/ γ-Al2O3 catalyst," App. Catal. A 109, pp. 77-96 (1994).

Laurent, et al., "Study of the hydrodeoxygenation of carbonyl, carboxylic and guaiacyl groups over sulfided CoMo/ γ-Al2O3 and NiMo/ γ-Al2O3 catalyst," App. Catal. A 109, pp. 97-115 (1994).

Leng, et al., "Catalytic Conversion of Palm Oil to Fuels and Chemicals," The Canadian Journal of Chemical Engineering, vol. 77, Feb. 1999, pp. 156-162.

Leonard, E.C., Polymerization—Dimer Acids, J. Am. Oil Chem. Soc., vol. 56, 1979, pp. 782A-785A.

Levenspiel, O., Chemical Reaction Engineering, Third Edition, John Wiley & Sons, Inc., 1999, pp. 207-239.

Lewis, R.J., Hawley's Condensed Chemical Dictionary, 12th Edition, 1993, p. 907.

List of Materials Considered by Dr. Michael T. Klein.

Long et al., "Noble Metal (Pt, Rh, Pd) Promoted Fe-ZSM-5 for Selective Catalytic Oxidation of Ammonia to N2 at Low Temperatures", Catalysis Letters, Mar. 2002, vol. 78, Nos. 1-4, pp. 353-357.

Long, et al., "A Simple Test to Detect Chlorophyll in Tallow," Presented before the 8th Annual Fall Meeting—A.O.C.S., Oil & Soap, 1935. (2 pages).

MacDonald, "Fuel From Fats," enerG Alternative Sources Magazine, Sep./Oct. 2011, 4 pages.

Mag, T., "Canola Seed and Oil Processing", Canola Council of Canada, 1994, 6 pages.

Mansfield Fuels, "Norfolk Southern Pens Deal with Dynamic Fuels and Mansfield Oil", http://www.mansfieldoil.com/latest-news-a-press/524-norfolk-southern-pens-deal-with-dynamic-fueis-and-mansfield-oil.html, Accessed Nov. 12, 2012, 2 pages.

Marker, T.L., "Opportunities for Biorenewables in Oil Refineries Final Technical Report," submitted to U.S. Department of Energy, Apr. 2005, 60 pages.

Miller, "Studies on Wax Isomerization for Lubes and Fuels, Zeolited and Related Microporous Materials: State of the Art in 1994," Studies in Surface Science and Catalysts, 1994, vol. 84, pp. 2319-2326.

Mirante et al., "Cloud point prediction of fuels and fuel blends," Fluid Phase Equilibria 180, 2001, pp. 247-255.

Moyse, "Graded Catalyst Systems to Combat Bed-Fouling Problems", Haldor Topsoe, Inc. 1996, 16 pages.

Nawar, W.W., Thermal Degradation of Lipids. A Review, J. Agr. Food Chem, vol. 17, No. 1, 1969, pp. 18-21.

(56) References Cited

OTHER PUBLICATIONS

N-dodecane Compound Summary, PubChem, National Center for Biotechnology Info., Sep. 16, 2004, http://pubchem.ncbi.nlm.nih.gov/summary/summary.cgi?cid=8182#x27.
Neste Oil, NExBTL Renewable Synthetic Diesel, Cal Hodge handout presented at Climate Action Team Technology Symposium, Sacramento, California, Jun. 27-28, 2006, available at http://www.climatechange.ca.gov/events/2006-06-27 28_symposium/presentations/ (last modified May 7, 2008).
Non-Final Office Action in U.S. Appl. No. 12/331,906 (Now U.S. Pat. No. 8,231,804) dated Oct. 21, 2011 (9 pages).
Non-Final Office Action in U.S. Appl. No. 13/466,813, dated Jul. 16, 2015 (9 pages).
Non-Final Office Action in U.S. Appl. No. 13/742,991 dated Jan. 16, 2014 (27 pages).
Non-Final Office Action in U.S. Appl. No. 13/742,991 dated Mar. 5, 2013 (13 pages).
Non-Final Office Action in U.S. Appl. No. 14/024,490 dated Jan. 17, 2014 (17 pages).
N-tetradecane Compound Summary, PubChem, National Center for Biotechnology Info., Sep. 16, 2004, http://pubchem.ncbi.nlm.nih.gov/summary/summary.cgi?cid=12389#x27.
Paschke, R.F. et al., Dimer Acid Structures. The Thermal Dimer of Methyl 10-trans, 12-trans, Linoleate, J. Am. Oil Chem. Soc., vol. 41, 1964, pp. 723-727.
Paschke, R.F., et al., Thermal Polymerization of Unsaturated Fatty Esters Normal Methyl Linoleate, J. Am. Oil Chem. Soc., 1949, pp. 278-283.
Patent Owner's Contingent Motion to Amend in Inter Partes Review No. IPR2013-00578 (U.S. Pat. No. 8,231,804) dtd May 27, 2014.
Patent Owner's Response in Inter Partes Review No. IPR2013-00578 (U.S. Pat. No. 8,231,804) dtd May 27, 2014.
PCT Preliminary Report; PCT/US2009/045404; International Bureau; dated Dec. 16, 2010; 9 pages.
Petition for Inter Partes Review(U.S. Pat. No. 8,231,804) dtd Sep. 10, 2013.
Petrocelli, F.P. et al., Modeling Lignin Liquefaction—Catalytic Hydroprocessing of Lignin-Related Methoxyphenols and Interaromatic Unit Linkages, Fuel Sci. & Tech., 5(1), 1987, pp. 25-62.
Plantenga et al., "Specialized guard-bed technology can improve resid unit operation", Oil & Gas Journal, Oct. 21, 1991, 74-78.
Plantenga, F. L., et al., "NEBULA": A Hydroprocessing Catalyst with Breakthrough Activity, Stud. Surf. Sci. Catal. vol. 145, 2003, pp. 407-410; http://dx.doi.org/10.1016/50167-2991(03)80246-X.
Pope et al., "A Study of Catalyst Formulations for Isomerization of C7 Hydrocarbons", Applied Catalysis A: General 233, 2002, pp. 45-62.
Prakash, "A Critical Review of Biodiesel as a Transportation Fuel in Canada", Mar. 25, 1998, 163 pages.
Proctor & Gamble, "Better Rendering, A Manual Prepared by Proctor & Gamble", 2nd Ed., 1967, pp. ix-xi, 1-21.
Properties of Isononane—High Quality Chemical Properties, Accessed at http://chemeo.com/cid/73-453-8 on Aug. 23, 2013 (2 pages).
Przybylski,R., "Canola Oil: Physical and Chemical Properties", Canola Council of Canada, 1998, 12 pages.
Rahimi et al., "Effect of Hydrotreating on the Stability of Synthetic Crude from Western Canada," Symposium on Stability and Oxidation Chemistry of Fuels, Dallas, Spring 1998, ACS Fuels 43 (1), pp. 13-17; Available for download at http://web.anl.gov/PCS/acsfuel/preprint%20archive/43_1_DALLAS_03-98.htm.
Ramin Abhari E-mail Correspondence with Hall Estill, Nov. and Dec. 2008. (Ex. 2017 in IPR2013-00578).
Rantanen, et al., "NExBTL—Biodiesel Fuel of the Second Generation," SAE Technical Paper 2005-01-3771 (published Oct. 24, 2005), 17 pages.
Register Entry for SG Publication No. 172045 dtd Jun. 9, 2011.
Relevant Pages of Syntroleum Report prepared by Vladimir Gruver (catalyst supplier and grade information redacted), 2007. (Ex. 2003 in IPR2013-00578).
Reply and Defense to Counterclaim, *Syntroleum Corp.* v. *Nest PTE. Ltd.*, No. 120 of 2013 (High Ct. Apr. 19, 2013) (Sing.).
Reproduction of Figure 5 of Iki.
Sandler, S., "Chemical and Engineering Thermodynamics," at 1-3, 324-33, 598-603 (3rd Ed. 1999).
Sanford et al., "Improved Catalyst Loading Reduces Guard Reactor Fouling", Oil & Gas Journal, Dec. 19, 1988, pp. 35-41.
Santana, et al., "Evaluation of Different Reaction Strategies for the Improvement of Cetane Number in Diesel Fuels," Fuel 85: 643-656 (2006).
Satterfield, C.N., Heterogeneous Catalysis in Industrial Practice, 2nd Edition, Sections 9.8-9.11, McGraw-Hill, Inc., NY (1991), pp. 375-389.
Senol, et al., Hydrodeoxygenation of aliphatic esters on sulphided NiMo/ $\gamma$-Al2O3 and CoMo/ $\gamma$-Al2O3 catalyst: The effect of water, Catalysis Today, 106 (2005), pp. 186-189.
Senol, et al., Hydrodeoxygenation of methyl esters on sulphided NiMo/ $\gamma$-Al2O3 and CoMo/$\gamma$-Al2O3 catalysts, Catalysis Today, 100 (2005), pp. 331-335.
SG Written Opinion; Application No. 201008935-7; Danish Patent and Trademark Office; dated Sep. 1, 2012; 18 pages.
Sharma, S.D., et al.; "Latent Heat Storage Materials and Systems: A Review"; International Journal of Green Energy; 2:1-56; 2005.
Sharp, D.W.A., The Penguin Dictionary of Chemistry, Second Edition, 1990, pp. 207, 263, 432, 433.
Sie, S.T., "Acid-Catalyzed Cracking of Paraffinic Hydrocarbons. 1. Discussion of Existing Mechanisms and Proposal of a New Mechanism," Ind. Eng. Chem. Res., vol. 31, No. 8, 1992, pp. 1881-1889.
Sie, S.T., "Acid-Catalyzed Cracking of Paraffinic Hydrocarbons. 2. Evidence for the Protonated Cyclopropane Mechanism from Catalytic Cracking Experiments" Ind. Eng. Chem. Res., vol. 32, No. 3, 1993, pp. 397-402.
Sie, S.T., "Acid-Catalyzed Cracking of Paraffinic Hydrocarbons. 3. Evidence for the Protonated Cyclopropane Mechanism from Hydrocracking / Hydroisomerization Experiments" Ind. Eng. Chem. Res., vol. 32, No. 3, 1993, pp. 403-408.
Simacek, et al., "Hydroprocessed rapeseed oil as a source of hydrocarbon-based biodiesel", Fuel 88, 2009, 456-460.
Sinha, et al., "Hydroisomerization of n-Alkanes over Pt-SAPO-11 and Pt-SAPO-31 Synthesized from Aqueous and Nonaqueous Media," Ind. Eng. Chem. Res., 1998, 37 (6), pp. 2208-2214.
Sixth Canadian Bioenergy R&D Seminar, Richmond, B.C., 1987 (19 pages).
Smejkal, et al., "Thermodynamic balance in reaction system of total vegetable oil hydrogenation", Chemical Engineering Journal 146 (2009) 155-160.
Smejkal, et al., Bibliographic Data for: "Thermodynamic balance in reaction system of total vegetable oil hydrogenation", Chemical Engineering Journal 146 (2009) 155-160.
Smith, et al., "Introduction to Chemical Engineering Thermodynamics," 5th Ed., 1996, pp. 526-531.
Song, et al., Temperature Programmed Retention Indices for GC and GC-MS of Hydrocarbon Fuels and Simulated Distillation GC of Heavy Oils, Analytical Advances for Hydrocarbon Research, 147-210, 2003.
Southwest Research Institute (SwRI) Status Report dated Apr. 1, 2008. (Ex. 2012 in IPR2013-00578).
Soveran et al., "The Effect on Diesel Engine Emissions with High Cetane Additives From Biomass Oils," Proc. American Chemical Society (Division of Fuel Chemistry) Meeting San Francisco, CA, Apr. 1992, pp. 74-85.
Spataru, "AGTANE (AGricultural ceTANE): An Economically Viable Bioenergy Product for Compression Ignited Engines", Fuel Chemistry Division Preprints, 2002, vol. 47(1), p. 365.
Spataru, "Is There a Future for Yellow Grease as a Fuel Additive?," Render, Feb. 2001, pp. 12-14.
Spataru, et al., "AGTANE (AGricultural ceTANE): An economically viable bioenergy product for compression ignited engines," 5th International Biomass Conference of the Americas Sep. 21, 2001, 2 pages.
SRI, "Sample Analyses Final Report" Southwest Research Institute, Oct. 31, 2008, 2 pps.

(56) References Cited

OTHER PUBLICATIONS

Standard Methods for the Analysis of Oils, Fats and Derivatives, 6th Ed., Part 1, pp. 96-108 (Pergamon Press 1979).
Statement of Claim, *Syntroleum Corp.* v. *Neste Oil Sing. PTE.*, No. 120 of 2013 (High Ct. Feb. 7, 2013) (Sing.).
Stork, W.H.J., "Molecules, catalysts and reactors in hydroprocessing of oil fractions", Hydrotreatment and Hydrocracking of oil fractions, 1997 Elsevier Science B.V., 41-67.
Stumborg et al., "Hydroprocessed Vegetable Oils for Diesel Fuel Improvement." Bioresources Technology, 1996, vol. 56, pp. 13-18.
Stumborg, et al., "Catalytic Conversion of Vegetable Oils to Diesel Additives," Energy from Biomass and Wastes XVI, pp. 721-738, 1993.
Syntroleum e-mail string dated Jul. 19, 2007 regarding use of Intertek PARC for pilot plant testing. (Ex. 2009 in IPR2013-00578).
Syntroleum Excel Spreadsheet containing GC test data of Exhibit 2004 dated May 31, 2007 (catalyst supplier and grade information redacted). (Ex. 2006 in IPR2013-00578).
Syntroleum Gas Chromatography ("GC") Test Report dated May 31, 2007 (catalyst supplier and grade information redacted). (Ex. 2004 in IPR2013-00578).
Syntroleum webpage, "Bio-Synfining—Dynamic Fuels Plant"; http://www.b2i.us/profiles/investor/fullpage.asp?BzID=2029&to=cp&Nav=O&LangID=1&s=0&ID=11923, Accessed Nov. 21, 2012, 4 pages.
Table 4a. U.S. Crude Oil and Liquid Fuels Supply, Consumption and Inventories, Dec. 2012, 1 pp.
Taylor et al., Modern Advanced Control Pays Back Rapidly, Hydrocarbon Processing, Sep. 2000 issue, pp. 47-50.
TCI America, "Material Safety Data Sheet—5-Methylnonane," 2010, 3 pages.
Tempier, et al., "Identifying Environmentally Preferable Uses for Biomass Resources," Ch. 4, (Mar. 31, 2004).
Tong, et al., "Flame Ionization Detector Response Factors for Compound Classes in Quantitative Analysis of Complex Organic Mixtures," Anal. Chem., 56:2124-2128 (1984). (Ex. 2026 in IPR2013-00578).
Transcript of Deposition of Dr. Michael T. Klein, taken May 13, 2014. (Ex. 2025 in IPR2013-00578).
Tyson et al., "Biomass Oil Analysis: Research needs and Recommendations," NREL Technical Report, Jun. 2004, 116 pages.
U.S. Appl. No. 12/331,906, filed Dec. 10, 2008(now U.S. Pat. No. 8,231,804).
U.S. Dept. of Agriculture—Oilseeds: World Markets and Trade, "Soybean Oil and Palm Oil Account for an Increasing Share of Word Vegetable Oil Consumption", (2003), 27 pages.
U.S. Natural Gas Wellhead Price data and graph from U.S. Energy Information Administration, released Nov. 30, 2012, 1 pp; Available for download at http://www.eia.gov/dnav/ng/ng_pri_sum_dcu_nus_m.htm.
U.S. Appl. No. 60/934,710, filed Jun. 15, 2007 (base provisional of U.S. Pub. No. 2008/0308458). (16 pages).
Vajo, et al., "Steady-State Decomposition of Ammonia on the Pt(110)-(1x2) Surface", The Journal of Physical Chemistry, 1986, vol. 90, No. 24, pp. 6531-6535.
Venkatachalam, et al., Kinetics of Oligomerization of Methyl Ester of Dehydrated Castor Oil Fatty Acid over Molybdenum Oxide on Silica-Alumina Catalyst in Comparison with the Thermal Oligomerization Process, J. Poly. Sci. Poly. Chem. Ed., vol. 22, 1984, pp. 3805-3814.
*Voter Verified* v. *Election Sys. & Software, Inc.*, 2011 U.S. Dist. LEXIS 6956; 2011 WL 250426 (M.D. FI. Jan. 25, 2011) (Ex. 2037 in IPR2013-00578).
Widmor, et al., "Prediction of the Freeze Point Temperature of Jet Fuel Using a Thermodynamic Model," Petroleum Chem. Div. Preprints, 47(3): 329-242 (2002).
Wong et al., "Conversion of Vegetable Oils and Animal Fats Into Paraffinic Cetane Enhancers for Diesel Fuels," Second Biomass Conference of the Americas: Energy, Environment, Agriculture, and Industry, 1995, pp. 901-910.
Wong, A., ARBO-TANE, The Green Diesel Fuel, Naval Stores Review 14-15 (Jul./Aug. 1991).
Wong, et al., Bio-Based Cetane Enhancer for Diesel Fuels, BioEnergy 1998: Great Lakes Regional Biomass Energy Program. (12 pages).
Wong, et al.; "Technical and Economic Aspects of Manufacturing Cetane-Enhanced Diesel Fuel from Canola Oil"; Bio-Oils Symposium; Saskatoon, Saskatchewan, Canada; Mar. 2-3, 1994. 15 pages.
Wong, Tall Oil-Based Cetane Enhancer for Diesel Fuel, in 79th Annual Meeting, Technical Section, Canadian Pulp and Paper Association, Preprints "A", A313-A318, held Jan. 26-27, 1993.
Zhang, et al., "High shear mixers: A review of typical applications and studies on power draw, flow pattern, energy dissipation and transfer properties," Chemical Engineering and Processing, 57-58 (2012), pp. 25-41.
Notice of Allowance in U.S. Appl. No. 14/997,285, dated Jan. 3, 2018 (8 pages).

\* cited by examiner

EVEN CARBON NUMBER PARAFFIN COMPOSITION AND METHOD OF MANUFACTURING SAME

CROSS-REFERENCE TO RELATED PATENT APPLICATIONS

This application is a Continuation of U.S. application Ser. No. 14/997,285, now U.S. Pat. No. 9,963,401, filed on Jan. 15, 2016, which is a Continuation of U.S. application Ser. No. 13/466,813, filed on May 8, 2012, which is a Divisional of U.S. application Ser. No. 12/331,906, now U.S. Pat. No. 8,231,804, filed on Dec. 10, 2008, all of which are incorporated herein by reference, in their entireties, for any and all purposes.

BACKGROUND OF THE INVENTION

1. Field of the Invention

The present invention relates to producing specialty materials and chemical intermediates from bio-renewable feedstocks such as animal fats, plant oils, algal oils, bio-derived greases, and tall oil fatty acid (hereafter referred to as biological feedstocks, or alternatively, fatty acids and/or glycerides depending upon the composition of the feedstock). Specifically, the present invention relates to predominantly even carbon number paraffin compositions in the $C_{12}$-$C_{24}$ range, and the catalytic hydrogenation/hydrogenolysis method used for its manufacture.

Paraffins in the $C_{12}$-$C_{24}$ range have useful applications as phase change material (PCM). The paraffins undergo solid-liquid phase transition in the about −9° C. (15° F.) to about 50° C. (120° F.). Heat is absorbed as the PCM paraffin melts and heat is released later when the PCM freezes. Fabricated systems that use PCM's as such are referred to as passive thermal storage devices. Due to relatively high latent heats of solid-liquid phase transition (referred to simply as latent heats hereafter), as well as compatibility with common material of construction and high stability, paraffins are considered particularly well-suited for PCM applications. Wall boards of a house impregnated with a PCM are an example of a passive thermal storage device. During a hot day, the PCM will absorb heat as it melts. Since there is no temperature change during phase transition, the surface in contact with the thermal storage device stays at constant temperature until all PCM therein has melted. The heat that would have made the house hot has thus been stored in the molten PCM. At night, as the temperatures get cooler, the molten PCM freezes and releases the heat thus preventing the home from getting cold. The melting-freezing cycles moderate the temperature of the space enclosed within the passive thermal storage device despite extreme night-day temperature swings outside. In general, PCMs are an effective way of storing thermal energy (e.g. solar, off-peak electricity, industrial waste heat), and reducing energy demand (e.g. for heating and air-conditioning).

The thermal storage capacity of the PCM is dictated by its latent heat. The higher the latent heat, the higher the thermal storage capacity of the PCM, and the smaller the required thermal storage device size/cost.

Table 1 provides the latent heats and melting points of paraffins. As observed therein, the latent heat for even carbon number paraffins is higher than the latent heat for odd carbon number paraffins of similar transition temperature. For example, n-heptadecane (carbon number 17) and n-octadecane (carbon number 18) melt in the 22-28° C. range. Whereas the latent heat of n-heptadecane is 215 kJ/kg and the latent heat for n-octadecane is 245 kJ/kg or 14% higher. In general, the even carbon number paraffin heats of fusion in the $C_{14}$-$C_{24}$ range are 10-16% higher than odd carbon number paraffins.

TABLE 1

Latent Heats and Solid-Liquid Transition Temperatures of Selected Paraffins

| Name | Carbon Number | Melting Point (° C.) | Latent Heat (kJ/kg) |
| --- | --- | --- | --- |
| n-Tetradecane | 14 | 4.5-5.6 | 231 |
| n-Pentadecane | 15 | 10 | 207 |
| n-Hexadecane | 16 | 18.2 | 238 |
| n-Heptadecane | 17 | 22 | 215 |
| n-Octadecane | 18 | 28.2 | 245 |
| n-Nonadecane | 19 | 31.9 | 222 |
| n-Eicosane | 20 | 37 | 247 |
| n-Heneicosane | 21 | 41 | 215 |
| n-Docosane | 22 | 44 | 249 |
| n-Tricosane | 23 | 47 | 234 |
| n-Tetracosane | 24 | 51 | 255 |

In addition to PCM applications, even carbon number $C_{12}$-$C_{24}$ paraffins are also used as chemical intermediates for linear alkyl benzene ($C_{12}$, $C_{14}$) and alkyenyl succinate ($C_{16}$, $C_{18}$), as well as lubricant/wax additives.

2. Brief Description of the Related Art

The commercially practiced synthesis of even carbon number n-paraffins involves ethylene oligomerization. Depending on the catalyst and reactor operating conditions, this process produces a distribution of linear alpha olefins in the $C_4$ to $C_{20}$+ range. Linear alpha olefins in the $C_4$-$C_8$ range are the main products of this process and are separated. These olefins are in high demand, mainly as comonomers for film-grade polyethylene. The $C_{10}$+ even carbon number olefins are sold as intermediates for specialty chemicals, or hydrogenated to produce even carbon number n-paraffins.

This ethylene oligomerization process for producing even carbon number paraffins is highly dependent on crude oil and natural gas prices. Furthermore, n-paraffins have to be sold at a premium to the olefins to justify the added cost of hydrogenating. These factors make the price and availability of n-paraffins thus produced highly variable.

Another method of producing n-paraffins is Fischer-Tropsch synthesis. The liquid product of this reaction is a broad distribution of even and odd carbon number paraffins, from $C_5$ to $C_{50}$+.

Naturally occurring fatty acids and esters may be hydrotreated to produce a hydrocarbon composition including even and odd carbon number paraffins as reported in prior art, namely: Wong, et. al. "Technical and Economic Aspects of Manufacturing Cetane-Enhanced Diesel Fuel from Canola Oil"; Bio-Oils Symposium, Saskatoon, Saskatchewan, Canada; March 1994. FIG. 2 of Wong et. al. includes typical gas chromatography/mass spectrometry (GC/MS) trace of hydrotreated canola oil wherein the relative heights of even and odd carbon number paraffins are similar, indicating presence of comparable concentrations of each. The prior art method for converting triglycerides and fatty acids to paraffins employs a fixed-bed catalytic reactor, packed with commercially available hydrotreating catalysts. These catalysts are cylindrical or three-fluted extrudates of alumina with nickel molybdenum or cobalt molybdenum sulfided metal activity. The typical equivalent diameter of these catalysts is from about 1.5 mm to about 2.0 mm.

The equivalent diameter is used to characterize non-spherical particles by size. Equivalent particle diameter of a non-spherical particle is defined as the diameter of a sphere having the same volume as the non-spherical particle. For a cylindrical catalyst of diameter D and length L, the equivalent particle diameter $D_p$ is expressed as $D_p=6(4/L+4/D)^{-1}$. For a three-fluted extrudate, the equivalent particle diameter expression is $D_p=6[2/L+5\pi/(D(\sin(60°)+1.25\pi)]^{-1}$.

The fatty acid/glyceride feed is hydrogenated and deoxygenated in the fixed bed reactor packed with commercial hydrotreating catalysts. As illustrated by Equations 1 and 2 for the example of triolein (oleic acid triglyceride), the deoxygenation is achieved by oxygen hydrogenolysis, decarboxylation (removal of $CO_2$), and decarbonylation (loss of CO).

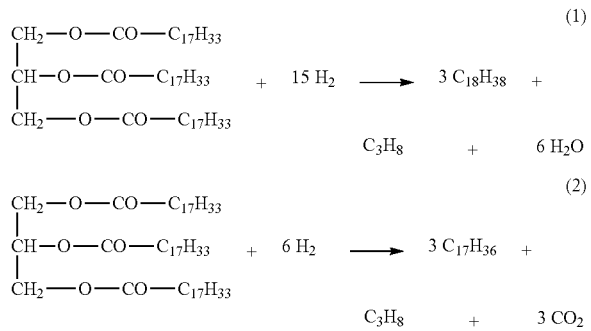

In both reactions, the glycerol backbone is converted to propane and double bonds are saturated. Since one carbon is removed from the fatty acids during decarboxylation and decarbonylation reactions (as illustrated in Equation 2), odd carbon number paraffins are formed from even carbon number naturally occurring fatty acids.

To this end, there is a need for even carbon number paraffin compositions and a selective process for producing even carbon number paraffins. In particular, the present invention is a process for converting biological feedstocks into even carbon number paraffin compositions.

DETAILED DESCRIPTION OF THE PREFERRED EMBODIMENTS

The present invention relates to even carbon number paraffin compositions and a method for producing such even carbon number paraffin compositions from biological feedstocks. Paraffin compositions of the present invention have superior properties as phase PCM material.

It has been discovered that hydrocarbon compositions with very high concentrations of even carbon number paraffins can be obtained from biological feedstocks. The products are produced by a single-step hydrogenation/hydrogenolysis process of biological feedstocks. One embodiment of the process is carried out using a bimetallic catalyst of about 10 to about 500 micron equivalent particle diameter. The shorter diffusion path length, more accessible pores, and lower intra-catalyst temperature gradients in the smaller catalyst system of the present invention reduce thermal decarboxylation and consequent co-production of odd number paraffins.

One embodiment of the process of the present invention is preferably carried out with the catalyst in the slurry phase. Commercially available catalyst extrudates may be ground and sieved to reduce the catalyst size to the preferred range of the present invention, from about 10 microns to about 400 microns, most preferably from about 30 microns to about 80 microns. Examples of the catalyst include but are not limited to nickel-molybdenum (NiMo), cobalt-molybdenum (CoMo), or nickel-tungsten (NiW) on alumina or alumina phosphate supports. Pre-ground catalyst extrudates are commercially available in both oxide and active sulfide forms. The metal oxide catalysts are activated by sulfiding.

Commercial bimetallic catalysts are also available as slurry grades and well-suited for the invention disclosed herein. Preferred examples include sponge metal catalysts such as Mo promoted Raney® Ni and Co (Raney® is the trade name of the Grace Davison sponge metal catalyst). Sponge metal catalysts are formed by leaching nickel-aluminum or cobalt-aluminum alloys with concentrated caustic (sodium hydroxide) solution to form hydrogen active metal of high surface area. These slurry catalysts are active as received, but may be sulfided to achieve the desired selectivity.

Supported slurry catalysts suitable for the process of this invention may be prepared by impregnating spray-dried alumina or modified alumina supports with solutions containing nickel, cobalt, molybdenum and/or tungsten compounds before calcining.

It should be understood by one of ordinary skill in the art that any such catalyst may be utilized in the present invention so long as the catalyst operates as described herein.

Figure 1:
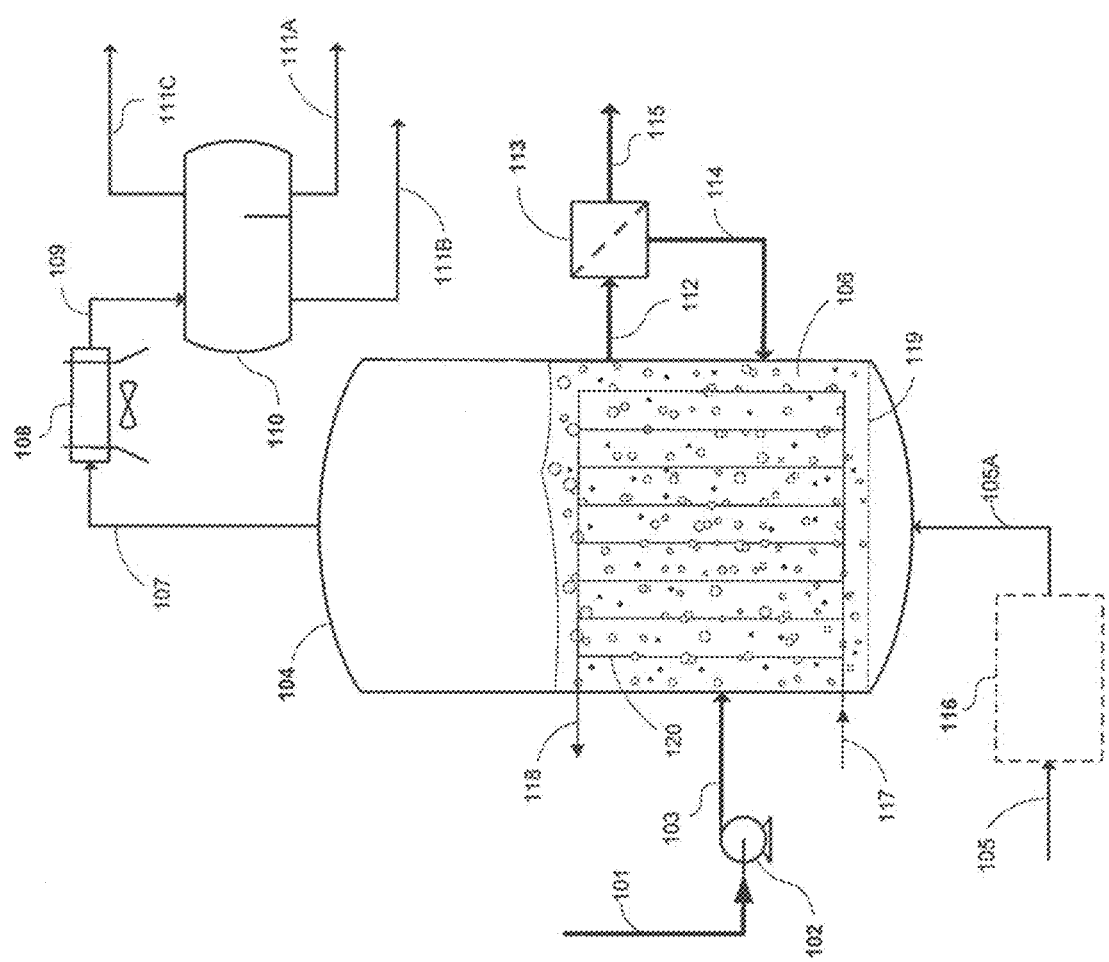
FIG. 1 is a schematic diagram of an embodiment of an operation of a continuous process in accordance with the present invention.

Referring now to the drawings and more particular to FIG. 1, shown therein is one embodiment of an operation of a process utilizing a continuous flow reactor constructed in accordance with the present invention. A biological feedstock 101 is pressurized to reactor pressure of about 200 psig to about 2,000 psig via pump 102. Preferred operating pressures for the slurry bubble column reactor are from about 400 to about 1,000 psig. The feed 101 comprises of vegetable oils, animal fats/greases, plant oils, tall oil fatty acid, and algal oils. Algal oils can be naturally occurring or produced in bioreactors. Pressurized liquid stream 103 enters a reactor 104.

The slurry reactor 104 is preferably a bubble column. The reactor catalyst loading is between about 1% and about 30% (dry bulk catalyst volume per total slurry volume), preferably between about 2% and about 20%. The catalyst particle size is from about 10 to about 400 microns, preferably from about 30 to about 80 microns. The throughput of the pressurized biological feed stock 103, is between about 0.1 and about 10 LHSV (volume feed per volume catalyst per hour), preferably between about 0.5 and about 5 LHSV. These parameters set the slurry reactor 104 volume for the design feed rate.

The pressurized liquid stream 103 reacts therein with hydrogen 105 which is optionally preheated through heater 116. The hydrogen-rich gas 105 preferably has a hydrogen concentration between 70 and 100 mol %, preferably between 80 and 99 mol %. The hydrogen-rich gas 105 is supplied at a rate of about 3,000 to about 10,000 SCF/bbl (volume gas per volume biological feedstock). The gas to feedstock ratio is preferably from about 4,000 SCF/bbl to about 8,000 SCF/bbl. The diameter of bubble column reactor vessel 104 is selected such that the gas flow rate is in the churn-turbulent regime from about 7 cm/s to about 40 cm/s, preferably from about 8 cm/s to about 12 cm/s. A heated hydrogen-rich gas 105A is dispersed through a sparger 119. The sparger may be of various configurations including but not limited to a ring-type sparger with multiple orifices, a sintered metal plate or sintered metal distributing pipe(s) or co-fed with the biological feedstock via a simple pipe distributor. In some embodiments the catalyst is dispersed in the slurry phase by mechanical agitation. The gas flow through the reactor 104 produces a uniform catalyst slurry 106. Alternatively, a side arm/downcomer (not shown) can also be deployed to recirculate de-gassed slurry to the reactor 104 which also aides catalyst distribution in the reactor 104. The biological feedstock converts into mainly even carbon number paraffins as it is diluted within the catalyst-paraffin slurry 106.

The heat of reaction is in part removed by evaporation of a boiler feed water 117 in cooling tubes/coils 120, producing steam 118. At the hydrodynamic regimes described herein, high heat removal may be achieved with cooling coil device 120 immersed in the reactor 104. Typical heat transfer coefficient for a steam-generating cooling coil is in the 40 to 200 Btu/hr-ft$^2$-° F. range. The reactor temperature is thus controlled between about 450° F. (232° C.) to about 750° F. (399° C.), preferably between about 600° F. (315° C.) and about 650° F. (343° C.). At these preferred temperatures, high pressure steam (greater than about 400 psig, and preferably greater than about 600 psig) may be produced and used for driving motors, generating electricity, and/or supplying process heat.

The extent of back-mixing within the bubble column depends to a large extent on the height-to-diameter ratio of the reactor. Typical columns have successfully been modeled as 1.1-1.9 ideal CSTR's in series. At the preferred reactor design conditions, the reactor liquid composition is mainly the paraffin, and the temperature very close to uniform.

The vapor product 107 from bubble column reactor 104 is cooled in air cooler 108 wherein byproduct water and light hydrocarbons condense. At operating pressures below 500 psig and temperatures above about 315° C. (600° F.), more than about 50% of the $C_{18}$-paraffin reaction product will vaporize and is condensed overhead with water and light hydrocarbons.

A three phase composition 109 is separated in separator drum 110. The water stream 111B and hydrocarbon 111A are thus separated from recycle hydrogen-rich gas 111C. In some embodiments, the hydrogen-rich gas 111C may be purified to remove some or all of the minor reaction byproducts such as ammonia, hydrogen sulfide, and carbon oxides. Recycle hydrogen-rich gas may then be combined with makeup hydrogen to form the reactor hydrogen-rich gas 105.

The slurry 106 is transported through conduit 112 to filter 113 to separate the catalyst from the reactor product. In some embodiments filter 113 is a cross-flow filter. In other embodiments, a hydrocyclone followed by a filter is used. It should be understood by one of ordinary skill in the art that any device capable of separating suspended solids from liquid may be used in the present invention. The catalyst slurry concentrate stream 114 returns to reactor 104, while the filtered paraffin product 115 exits the reactor system. Product streams 115 and 111B include equal to or greater than about 75 wt % even carbon number paraffins in the $C_{12}$-$C_{24}$ range. Preferably, the product streams comprise of equal to or greater than about 80 wt % even carbon number paraffins. In some embodiments, the product stream may undergo further processing such as distillation to recover the even carbon number paraffin products.

In other embodiments of the present invention, a plurality of reactors are employed to divide the hydrogenation/hydrogenolysis load over two or more reactors. Those skilled in the art will recognize that the reactors-in-series configuration is used in back-mixed reactor systems to achieve higher conversion at same or lower total reactor volume.

Figure 2:
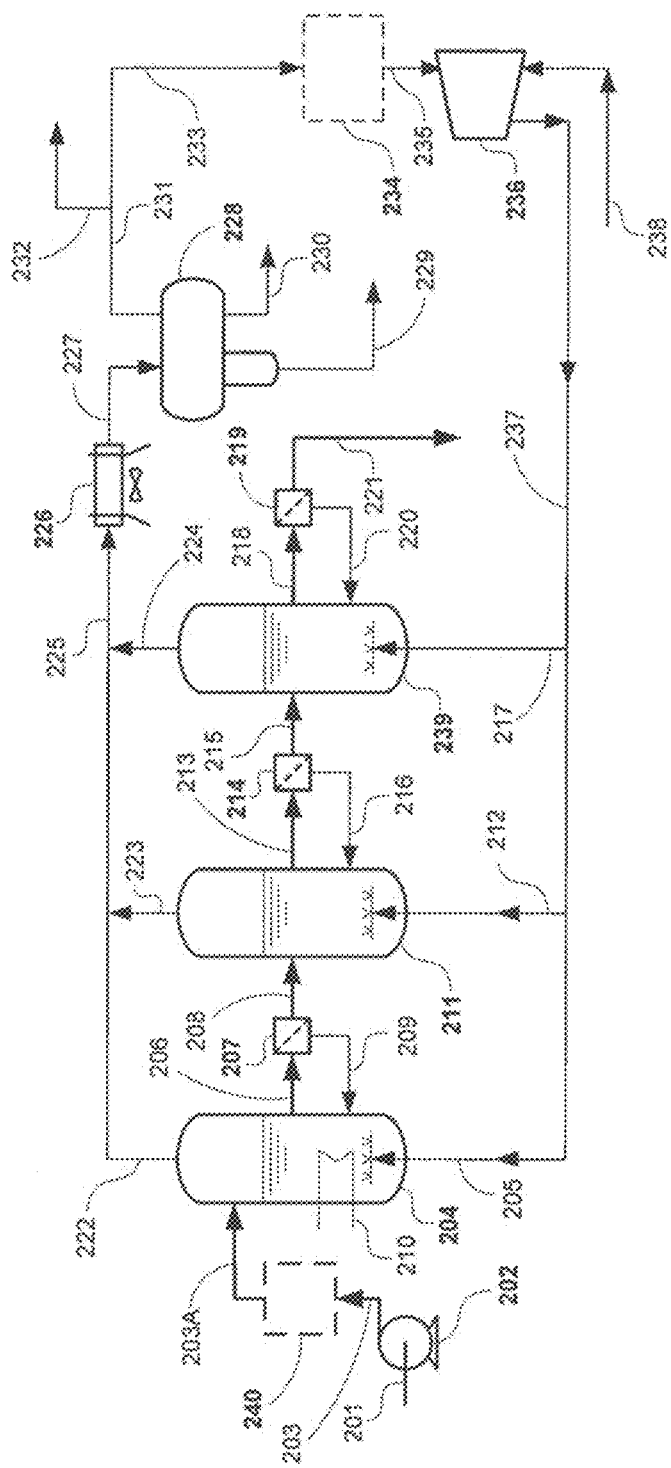
FIG. 2 is a schematic diagram of an embodiment of an operation of a series-reactor process in accordance with the present invention.

Referring now to FIG. 2, biological feedstock 201 is pressurized to the reactor system pressure in pump 202. The reactor system pressures are in the same range previously specified herein. The reactor system further contains catalyst of type and size specified in the detailed description of the invention. The pressurized feed 203 is optionally heated in heater 240. The preheated feed 203A enters the first stage reactor 204 wherein partial conversion occurs in the catalyst slurry phase. Hydrogen-rich gas 205 is introduced into slurry bubble column reactor 204 through a sparger device (not shown) at the rates previously specified herein. Reactor 204 is equipped with cooling coils 210 to maintain the reactor at the desired temperature range previously specified. The extent of feed conversion in reactor 204 is about 10% to about 90%, preferably about 30% to about 60%. Stream 206, the partially converted product including paraffin, biological feedstock, and reaction intermediates such as fatty alcohols, fatty acids, and olefins, is filtered through filter 207 to separate the catalyst. The catalyst rich slurry 209 is returned to the reactor 204 while the filtered, partially converted product 208 flows to second stage reactor 211.

Typically, a reactor 211 operates under the same temperature and gas-to-oil ratio as the reactor 204. In some embodiments the reactor 211 operates at a higher temperature than the reactor 204. In some embodiments, the pressure in reactors 211 and 239 are lower than the reactor 204 to facilitate filtrate flow from the reactor 204 to the reactor 211, and from the reactor 211 to the reactor 239. After undergoing reaction with hydrogen provided by gas stream 212, a partially converted slurry 213 undergoes solid-liquid separation in a filter 214. A catalyst rich slurry 216 is returned to the reactor 211 while the partially converted stream 215 is transferred to the reactor 239. The total extent of feed conversion in the reactor 211 is about 30% to about 95%, preferably between about 50% and about 80%.

Hydrogen is supplied to the reactor 239 from the gas stream 217. The total feed conversion achieved in this slurry bubble column reactor is between about 80% and about 100%, preferably at or very near about 100% feed conversion. The temperature, pressure, and gas-to-oil ratio are in the same range described previously. However in some embodiments, the reactor 239 is operated at a higher temperature than the reactors 204 and 211. A paraffin-catalyst slurry stream 218 is filtered in a filter 219 to supply a product stream 221 and returning high-solids slurry stream 220 to the reactor 239. The product 221 includes equal to or greater than about 75 wt % even carbon number paraffins in the $C_{12}$-$C_{24}$ range. Preferably, the product stream 221 comprises of equal to or greater than about 80 wt % even carbon number paraffins in the $C_{12}$-$C_{24}$ range.

The off gas from the three slurry bubble column reactors in series, streams 222, 223 and 224, are combined to form a vapor stream 225. The vapor stream 225 is cooled in a condenser 226 to a temperature from about 60° F. (15.5° C.) to about 160° F. (71° C.), preferably from about 80° F. (27° C.) to about 140° F. (60° C.). A three phase stream 227 enters drum 228 where the stream 227 is separated into a water phase 229, a light hydrocarbon phase 230 and a gas phase 231. The gas phase 231 is rich in hydrogen. The other components of the gas phase 231 include propane, other light hydrocarbons, and minor byproducts described previously. The hydrogen-rich gas stream may be partially purged (stream 232) with the rest recycled as stream 233. The aforementioned impurities may be removed in a hydrogen purification unit 234. The hydrogen purification unit 234 is typically a scrubber used to remove ammonia and hydrogen sulfide. A purified hydrogen-rich stream 235 is then combined with makeup hydrogen 238 in recycle compressor 236. A recompressed hydrogen-rich gas 237 is used to supply each of the slurry bubble column reactors.

Figure 3:
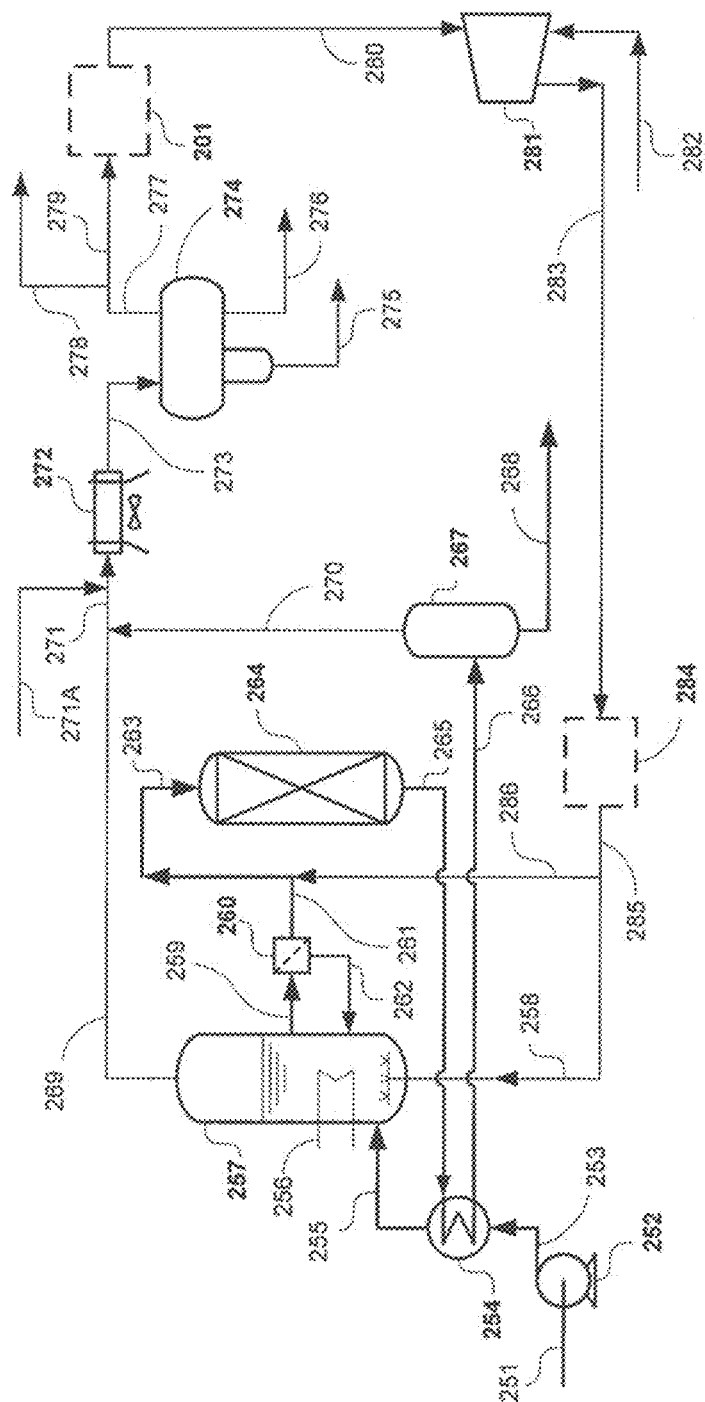
FIG. 3 is a schematic diagram of an alternative embodiment of an operation of a series-reactor process in accordance with the present invention.

In an alternative embodiment of an operation of a reactors-in-series process of the present invention, a slurry bubble column reactor containing catalyst of the type and size previously described herein may be followed by a fixed-bed reactor. Referring to FIG. 3, the biological feedstock 251 is pressurized by pump 252 to the reactor system pressure previously specified herein. The pressurized biological feedstock is heated by the reactor feed-effluent exchanger 254. A heated stream 255 enters a slurry bubble column reactor 257 where a catalyst of the type and size-range previously described herein is suspended in the slurry phase by sparging of hydrogen-rich gas 258. Reactor 257 is equipped with cooling coils 256 to control the temperature at target value within the range previously specified herein. A partially converted effluent slurry 259 is processed through filter 260. A catalyst rich slurry 262 is returned to the reactor 257 while a filtered partially converted product 261 is transferred to a fixed-bed reactor 264 for achieving full conversion. Before entering the reactor 264, the liquid feed is mixed with optionally preheated hydrogen 286. A combined feed 263 trickles through the fixed-bed reactor 264 wherein the partially converted feedstock and reaction intermediates are fully converted to a predominately even carbon number paraffin composition. The fixed-bed reactor 264 is operated adiabatically and the temperature is allowed to rise within the preferred range previously specified herein. A reactor effluent 265 is partially cooled in exchanger 254. A partially cooled product 266 enters high pressure separator 267 wherein the hydrogen-rich vapor stream 270 is separated from a mainly even carbon number paraffinic liquid product 268. The liquid product 268 may be further processed through distillation to recover the desired even carbon number paraffin composition previously specified herein.

The hydrogen-rich gas streams 270 and 269, from the high pressure separator 267 and the slurry bubble column reactor 257 respectively, are combined to form vapor stream 271. Water 271A is added to vapor stream 271 to wash any deposits that may form upon condensation in a condenser 272. A cooled stream 273 is a three phase composition which is separated in drum 274. The liquid fractions include byproduct water 275 and light hydrocarbons 276. A hydrogen-rich gas 277 is partially purged as stream 278. The rest of the gas, stream 279 is optionally treated in purification unit 290 to remove ammonia, hydrogen sulfide, and other byproducts of the hydrogenation/hydrogenolysis reaction. A purified hydrogen-rich gas 280 is combined with makeup hydrogen 282 in recycle compressor 281. A recompressed hydrogen-rich gas 283 is optionally heated in heater 284 before supplying the slurry bubble column 257 and the fixed-bed reactor 264.

The slurry catalyst reaction may also be conducted in batch mode. This may be a preferable embodiment when large volume production is not sought, or when the paraffin products from different feed stocks need to be segregated.

Figure 4:
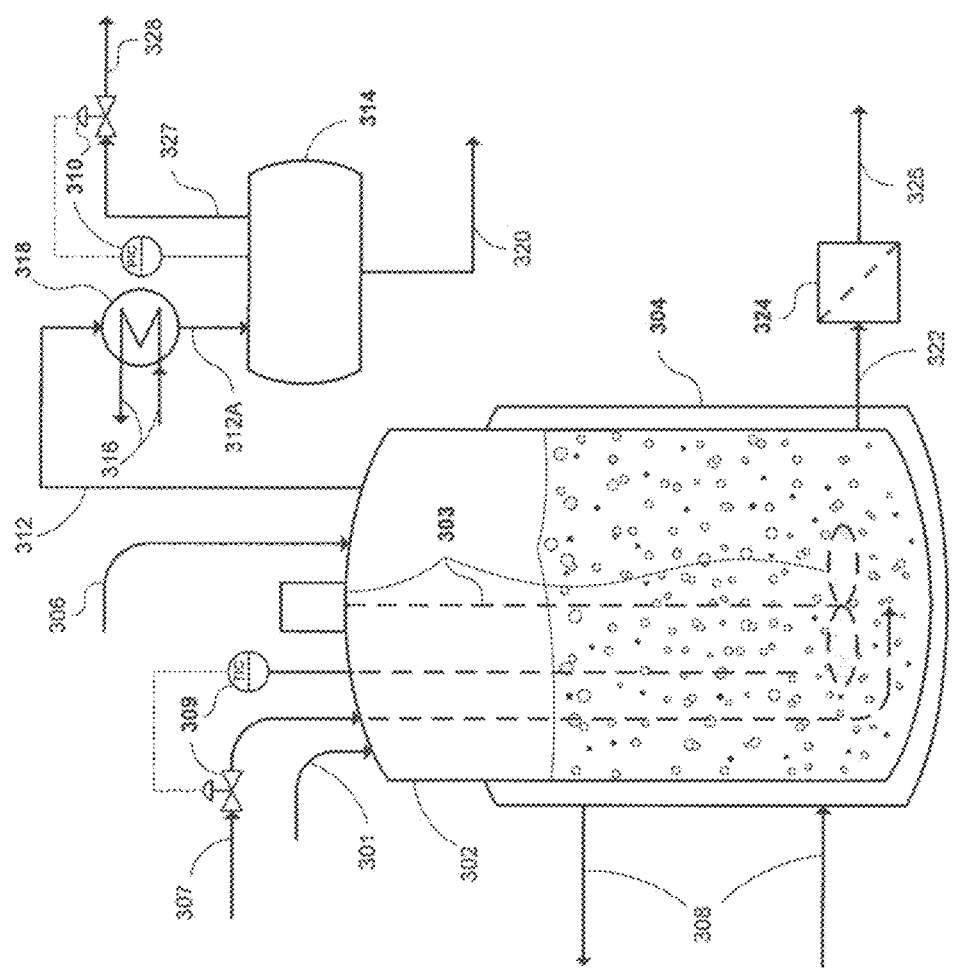
FIG. 4 is a schematic diagram of an embodiment of an operation of a batch process in accordance with the present invention.

Referring to FIG. 4, a biological feedstock 301 is charged to a batch stirred reactor 302. The reactor 302 is equipped with an agitator assembly 303 for suspending solids and dispersing gas, and a jacket 304 for heat transfer. A slurry catalyst 306 is then added to the reactor 302. The catalyst is of the type and size-range previously described herein. The reactor is then purged and pressurized with hydrogen 307 to the target operating pressure. Pressure ranges described previously for the continuous flow reactor embodiments are applicable to the batch reactor embodiment as well. These preferred pressures are from about 400 psig to about 1,000 psig.

The reactor 302 is then heated to a target operating temperature in the range previously described for the continuous reactor embodiments, preferably between 450° F. (232° C.) and 650° F. (343° C.). The operating temperatures may be achieved by circulation of a heat transfer fluid 308 through the reactor jacket 304. Once at target temperature, the heat transfer fluid 308 is used for cooling. The hydrogen 307 supply rate is used to limit the release of reaction heat through a temperature control loop 309. In some embodiments, the hydrogen flow rate is maintained constant and the reactor pressure is controlled through a back pressure control loop 310, while temperature is controlled through circulation rate of the heat transfer fluid. In some embodiments, reactor 302 is equipped with a cooling coil (not shown) to increase heat removal and shorten batch cycle.

The batch reactor is equipped with piping 312, 312A, and condenser 318. Condensable byproducts of the hydrogenation/hydrogenolysis reaction which occurred in reactor 302, light hydrocarbons and water, are thus collected in drum 314 after cool-down with coolant 316 in condenser 318. Upon completion of the reaction, when no more $H_2$ consumption is observed, the reactor 302 is cooled to about 140° F. (60° C.) to about 160° F. (71° C.) and the products and byproducts are drained out through conduits 320 (water, followed by light hydrocarbons) and 322 (main paraffin product). Most of the catalyst settles to the bottom of reactor 302 after agitation has been turned off, for reuse in the next batch. The suspended catalyst fines are removed from the n-paraffin product through filter 324. Sintered metal or cartridge elements may be used for catalyst filter 324. A filtered product 326 has the same even carbon number paraffin composition previously described in the continuous flow reactor embodiments of the present invention.

In order to further illustrate the present invention, the following examples are given. However, it is to be understood that the examples are for illustrative purposes and are not to be construed as limiting the scope of the subject invention.

EXAMPLES

Example 1—Hydrogenation/Hydrogenolysis of Canola Oil with 1/16" Trilobe Catalyst Extrudates ($D_p$~1.2 mm) in a Fixed-Bed Reactor The present example demonstrates the conversion of a biological feedstock, canola oils, into paraffinic compositions using standard-size catalyst extrudates. A 100 cc isothermal tubular reactor was filled with 80 cc of a commercially available NiMo catalyst (purchased from Catalyst Trading Corporation, Houston, Tex.) of 1.2 mm equivalent particle diameter, and 70-100 mesh glass beads. The catalyst was sulfided in the presence of hydrogen with dimethyl disulfide at two hold temperatures: 6 hours at 400° F. and 12 hrs at 650° F. Hydrogen sulfide break-through was confirmed before the temperature was raised from 400° F. (204° C.) to 650° F. (343° C.) at 50° F./hr. After sulfiding, the reactor was cooled to 400° F. (204° C.).

Next a fatty triglyceride feed was introduced to the isothermal reactor. The reactor was slowly heated to 650° F. to achieve full conversion of the triglyceride feed to a paraffin composition. The reactor temperature was further increased to 700° F. (371° C.) to maintain good catalyst activity at 80 cc/hr feed rate (1.0 hr$^{-1}$ LHSV). Canola oil feedstock was then introduced at these reactor conditions.

Figure 5:
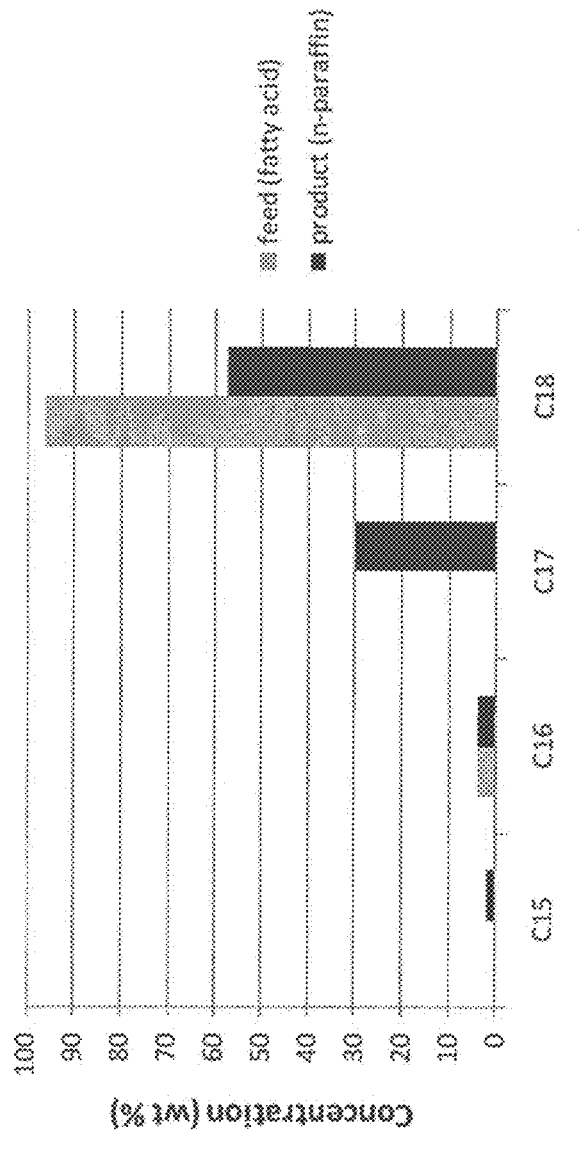
FIG. 5 is a bar graph summarizing the results of Example 1.

The product was analyzed using a gas chromatography (GC) method involving calibration with n-paraffin standards. The results of feed conversion to paraffins are summarized in FIG. 5. As observed therein, a significant percent of $C_{17}$ paraffins was produced from decarbonylation/decarboxylation of $C_{18}$ fatty acids. The overall concentration of even carbon number paraffins was only 61 wt %.

Example 2—Hydrogenation/Hydrogenolysis of Canola Oil with Crushed and Sieved Catalyst ($D_p$=30-80 Micron) in Slurry Reactor The catalyst used in Example 1 was discharged from the reactor, crushed, and sieved into a 30-80 micron particle-size cut. Ten (10) grams of the 30-80 micron cut of the ground catalyst was combined with 300 g of canola oil in a 1 liter Autoclave stirred-reactor. The agitation was set at 1000 rpm. The reactor was purged with $N_2$ before starting $H_2$ flow at 3 L/min. The reactor was controlled at 500 psig pressure. The temperature was ramped at 1° F./min to hold temperatures of 450° F. (232° C.), 500° F. (260° C.), 550° F. (288° C.), and 600° F. (316° C.). Liquid samples were obtained at each hold temperature and analyzed by GC. The hold times were 20 hrs at 450° F. (232° C.), 5 hrs at 500° F. (260° C.), 23 hrs at 550° F. (288° C.), and 19 hrs at 600° F. (316° C.).

Figure 6:
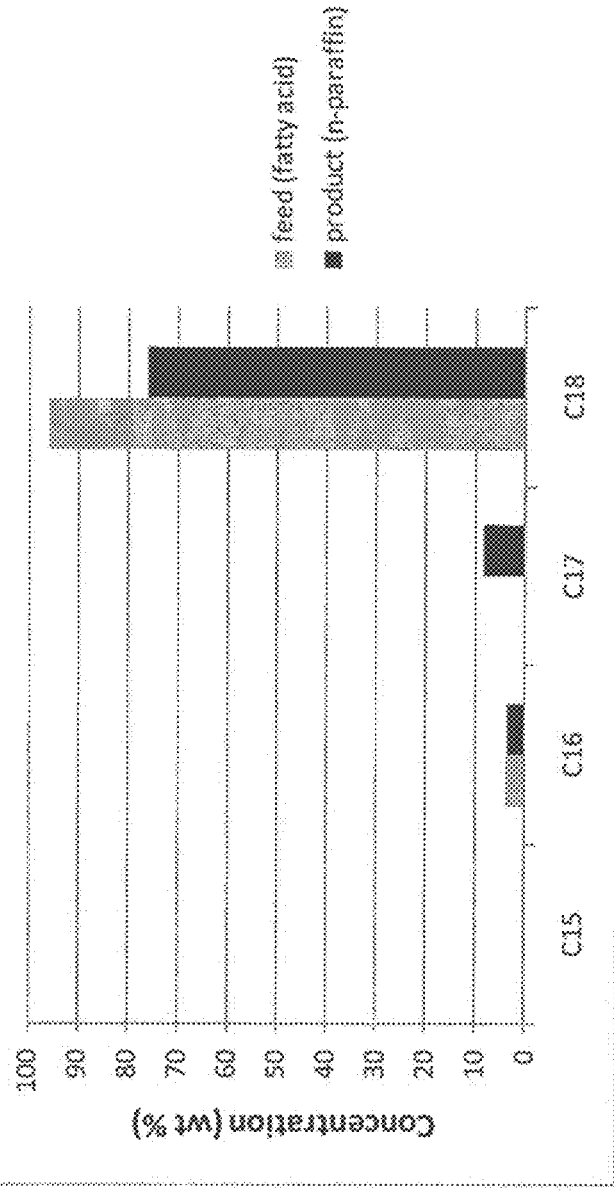
FIG. 6 is a bar graph summarizing the results of Example 2.

The results of the slurry catalyst conversion reaction are summarized in FIG. 6. It is thus observed that most of the $C_{18}$ and $C_{16}$ fatty acids in the canola oil were converted to $C_{18}$ and $C_{16}$ paraffins, suggesting a high selectivity for the oxygen hydrogenolysis mechanism and low decarboxylation/decarbonylation. The overall concentration of even carbon number paraffins was 80 wt %.

Example 3—Even Carbon Number Paraffin Composition from Rapeseed Oil

Rapeseed oil was the third largest source of vegetable oil in the world (USDA year 2000 statistics), behind palm and soybean oils. The oil yield from rapeseed is 40-50%, compared to only 20 percent for soybeans. Table 2 summarizes the fatty acid profile of representative biological feedstocks.

TABLE 2

Fatty Acid Composition of Several Common Biological Feedstocks [1-5]

| | Saturated Acids | | | | | | | Mono-Unsaturated Acids | | | Poly-Unsaturated Acids | |
|---|---|---|---|---|---|---|---|---|---|---|---|---|
| | | | | | | | | | | Eicosenic/ | | |
| | | | | | | | Eicosenic/ | | | | | |
| | Caprylic C8:0 wt % | Capric C10:0 wt % | Lauric C12:0 wt % | Myristic C14:0 wt % | Palmitic C16:0 wt % | Stearic C18:0 wt % | Behenic C20:0/C22:0 wt % | Palmeic C16:1 wt % | Oleic C18:1 wt % | Beheneic C20:1/C22:1 wt % | Linoleic C18:2 wt % | Linolenic C18:3 wt % |
| Animal fats | | | | | | | | | | | | |
| Chicken Fat | — | — | — | — | 7 | 2 | — | — | 69 | — | 17 | — |
| Beef Tallow | — | — | 0.2 | 2-3 | 24-30 | 21-26 | 0.4-1 | — | 39-43 | 0.3 | 2-3 | 1 |
| Yellow Grease | — | 3 | 3 | 1-11 | 23-27 | 10-12 | — | 1 | 29-50 | — | 2-15 | 1 |
| Choice White Grease | — | 7 | 3 | 9 | 25 | 12 | — | — | 27 | — | 1-3 | 1 |
| Lard (pork fat) | — | — | — | 1-2 | 25-30 | 12-16 | — | 2-5 | 41-51 | 2-3 | 4-22 | 0.2 |
| Vegetable Oils | | | | | | | | | | | | |
| Soybean Oil | — | — | — | 0.3 | 7-11 | 3-6 | 5-10 | 0-1 | 22-34 | — | 50-60 | 2-10 |
| Corn Oil | — | — | — | 0-2 | 8-11 | 1-4 | — | 1-2 | 28-50 | 0-2 | 34-58 | 1 |
| Cottonseed Oil | — | — | — | 0-3 | 17-23 | 1-3 | — | — | 23-41 | 2-3 | 34-55 | 1 |
| Canola Oil | — | — | — | — | 4 | 2 | — | — | 62 | — | 22 | 10 |
| Coconut Oil | 5-9 | 4-10 | 44-51 | 13-18 | 7-10 | 1-4 | — | — | 5-8 | — | 1-3 | — |
| Sunflower Oil | — | — | — | — | 6-7 | 4-5 | 1.4 | — | 19 | — | 68-69 | 0.3-1 |
| Palm Oil | — | — | — | 1-6 | 32-47 | 1-6 | — | — | 40-52 | — | 2-11 | — |
| Palm Kernel Oil | 2-4 | 3-7 | 45-52 | 14-19 | 6-9 | 1-3 | 1-2 | 0-1 | 10-18 | — | 1-2 | — |
| Rapeseed (High Eurcic) | — | — | — | — | 2-5 | 1-2 | 0.9 | 0.2 | 10-15 | 50-60 | 10-20 | 5-10 |

[1] http://www.scientificpsychic.com/fitness/fattyacids.html
[2] Kinast, J. A. March 2003, "Production of Biodiesel from Multiple Feedstocks and Properties of Biodiesel/Diesel Blends, NREL/AR-510-31460
[3] Tyson, K. S., NREL Presentation "Biodiesel for New England" Mar. 26, 2003
[4] Food Fats and Oils, Institute of Shortening and Edible Oils, Ninth Edition 2006
[5] a "—" in a cell means that this constituent is not present As observed therein, rapeseed oil consists of 50-60 wt % $C_{22}$ fatty acids with the balance mainly $C_{18}$ fatty acids. According to the inventive conversion process disclosed herein, rapeseed oil will produce an even carbon number composition comprising of a ratio of about 1:1 to 1.5:1 $C_{22}$:$C_{18}$ n-paraffins. This composition is useful as a PCM in construction or textile/clothing application for high temperatures, including desert climates when day times can surpass 44° C. (melt point of $C_{22}$ paraffin), and night times below 28° C. (freeze point of $C_{18}$ paraffin). The high temperature phase transition makes this PCM composition well suited for computer cooling applications (i.e. heat sink or cooling pad under the computer) as well.

Example 4—Even Carbon Number Paraffin Compositions from Palm Oil and Palm Kernel Oil Palm oil recently surpassed soybean oil as the largest volume plant oil produced in the world. Whereas palm oil itself is derived from the fruit of the palm tree, the palm kernel oil is extracted from the fruit's seeds. Referring to Table 2, palm oil consists of about 40 wt % $C_{16}$ fatty acids, with the balance mainly $C_{18}$ fatty acids. According to the method of the present invention, the palm oil is converted to a mainly even carbon number paraffin composition in the $C_{16}$-$C_{18}$ range with $C_{18}$:$C_{16}$ weight ratio of about 1.5:1. The composition is useful as a PCM for construction and textile/clothing applications in the 18° C. to 28° C. range.

Referring to Table 2, palm kernel oil has a fatty acid composition of about 45-52 wt % $C_{12}$, 14-19 wt % $C_{14}$, 6-9 wt % $C_{16}$, and 11-17 wt % $C_{18}$. According to the present invention, the biological feedstock is converted to a mainly even carbon number n-paraffin composition including $C_{12}$, $C_{14}$, $C_{16}$, and $C_{18}$ components. The n-paraffin composition may be distilled to yield a $C_{12}$/$C_{14}$ composition suitable for very low temperature PCM applications (such as for bridge warmers and dive suites) or as chemical intermediates (such as for producing linear alkyl benzenes).

Figure 7:
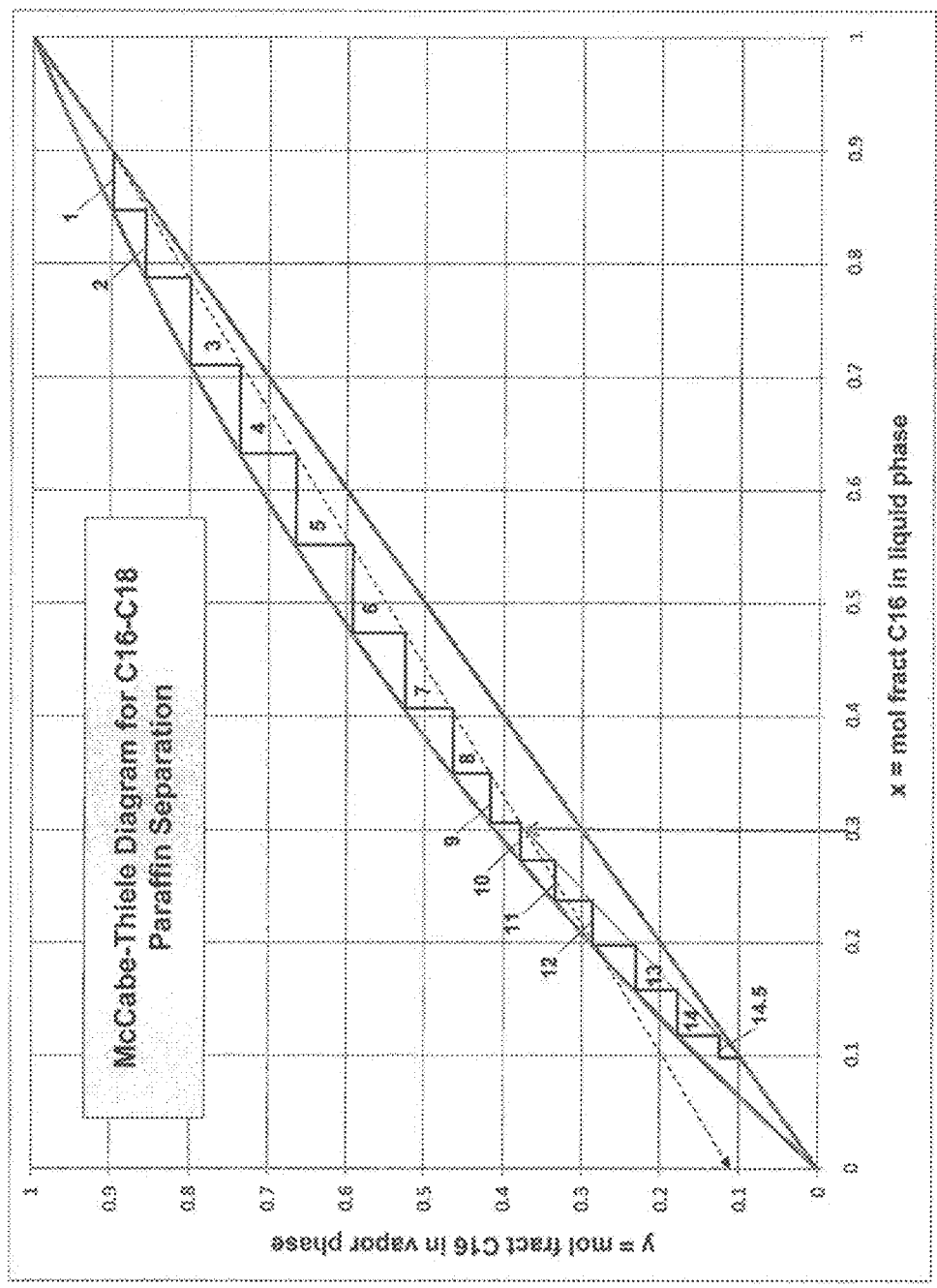
FIG. 7 is a McCabe-Thiele diagram for $C_{16}$-$C_{18}$ paraffin separation.

Example 5—Separation of Even Carbon Number Paraffins Derived from the Method of the Present Invention The method of the present invention may be used to convert most animal fats into a composition with approximately 30 mol $C_{16}$ n-paraffins and the balance mainly $C_{18}$ paraffin. Vacuum distillation is a well understood and broadly practiced separation technology. At 20 torr pressure, the vapor-liquid equilibrium (VLE) constants ("K-values") for n-octadecane and n-hexadecane are 1.34 and 0.82 respectively (computed using HYSYS simulation software's Peng-Robinson thermodynamic model). These K-values may be used to generate the equilibrium curve of FIG. 7. Distillation column operating lines have been added according to the McCabe-Thiele methodology as disclosed in prior art, namely, Foust et. al. *Principles of Unit Operations*, 2$^{nd}$ Ed.; John Wiley & Sons: New York, 1980; Chapter 7. According to McCabe-Thiele procedure for distillation column design, with a reflux ratio of 6.5, or 30% higher than minimum reflux, a separation yielding 90 mol % purity $C_{18}$ and $C_{16}$ n-paraffin products requires 14.5 theoretical stages. Assuming 73% tray efficiency, the vacuum tower requires 20 actual trays.

While the $C_{18}$ product of the separation can be sold as a PCM for narrow temperature control applications, the $C_{16}$ n-paraffin (n-hexadecane or cetane) has other markets. One large volume application is diesel fuel additive. Another use of linear $C_{16}$ hydrocarbons is as intermediates for specialty chemicals including alkenyl succinates for paper coatings.

The analysis of this example shows that the even carbon number compositions of the present invention, such as those derived from animal fats/greases, are well suited for producing chemicals using conventional separation techniques.

While the compositions and methods of this invention have been described in terms of preferred embodiments, it will be apparent to those of skill in the art that variations may be applied to the process described herein without departing from the concept and scope of the invention. All such similar substitutes and modifications apparent to those skilled in the art are deemed to be within the scope and concept of the invention as it is set out in the following claims.

What is claimed is:

1. A composition comprising paraffins falling in the $C_{12}$-$C_{24}$ range, wherein:
   the composition is undistilled;
   at least 75 wt % of the composition comprises even carbon number paraffins;
   the paraffins and the even carbon number paraffins are produced from a renewable biological feedstock by a process comprising hydrogenation and hydrogenolysis; and
   the even carbon number paraffins comprise n-dodecane and n-tetradecane.

2. The composition of claim 1, wherein the even carbon number paraffins further comprise n-hexadecane and n-octadecane.

3. The composition of claim 1, wherein at least 80 wt % of the composition is even carbon number paraffins.

4. The composition of claim 1, wherein the renewable biological feedstock is selected from the group consisting of vegetable oils, plant oils, algal oils, animal fats, tall oil fatty acid, products of the food industry, and a combination of any two or more thereof.

5. The composition of claim 1, wherein the renewable biological feedstock is selected from the groups consisting of soybean oil, corn oil, cottonseed oil, canola oil, coconut oil, sunflower oil, palm oil, palm kernel oil, rapeseed oil, and a combination of any two or more thereof.

6. The composition of claim 1, wherein the renewable biological feedstock is selected from the group consisting of soybean oil, canola oil, palm oil, palm kernel oil, rapeseed oil, and a combination of any two or more thereof.

7. The composition of claim 1, wherein the renewable biological feedstock comprises palm oil.

8. A diesel fuel comprising the composition of claim 1.
9. A diesel fuel comprising the composition of claim 2.
10. A diesel fuel comprising the composition of claim 3.
11. A diesel fuel comprising the composition of claim 4.
12. A diesel fuel comprising the composition of claim 5.
13. A diesel fuel comprising the composition of claim 6.
14. A diesel fuel comprising the composition of claim 7.

15. A composition comprising paraffins falling in the $C_{12}$-$C_{24}$ range, wherein:
   the composition is undistilled;
   at least 80 wt % of the composition comprises even carbon number paraffins;
   the paraffins and the even carbon number paraffins are produced from a renewable biological feedstock by a process comprising hydrogenation and hydrogenolysis over a bimetallic catalyst; and
   the even carbon number paraffins comprise n-hexadecane and n-octadecane.

16. The composition of claim 15, wherein the even carbon number paraffins further comprise n-dodecane and n-tetradecane.

17. The composition of claim 15, wherein the renewable biological feedstock is selected from the group consisting of vegetable oils, plant oils, algal oils, animal fats, tall oil fatty acid, products of the food industry, and a combination of any two or more thereof.

18. The composition of claim 15, wherein the renewable biological feedstock is selected from the groups consisting of soybean oil, corn oil, cottonseed oil, canola oil, coconut oil, sunflower oil, palm oil, palm kernel oil, rapeseed oil, and a combination of any two or more thereof.

19. The composition of claim 15, wherein the renewable biological feedstock is selected from the group consisting of soybean oil, canola oil, palm oil, palm kernel oil, rapeseed oil, and a combination of any two or more thereof.

20. The composition of claim 15, wherein the renewable biological feedstock comprises palm oil.

21. A diesel fuel derived from the composition of claim 15.

22. A diesel fuel derived from the composition of claim 16.

* * * * *

UNITED STATES PATENT AND TRADEMARK OFFICE
CERTIFICATE OF CORRECTION

PATENT NO. : 10,717,687 B2
APPLICATION NO. : 15/973064
DATED : July 21, 2020
INVENTOR(S) : Ramin Abhari et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 128 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*